US012672823B2

(12) United States Patent
Toth et al.

(10) Patent No.: US 12,672,823 B2
(45) Date of Patent: Jul. 7, 2026

(54) MONITORING PHYSIOLOGIC PARAMETERS FOR TIMING FEEDBACK TO ENHANCE PERFORMANCE OF A SUBJECT DURING AN ACTIVITY

(71) Applicant: LifeLens Technologies, Inc., Ivyland, PA (US)

(72) Inventors: Landy Toth, Doylestown, PA (US); Robert S. Schwartz, Inver Grove Heights, MN (US)

(73) Assignee: LifeLens Technologies, Inc., Ivyland, PA (US)

( * ) Notice: Subject to any disclaimer, the term of this patent is extended or adjusted under 35 U.S.C. 154(b) by 726 days.

(21) Appl. No.: 17/056,573

(22) PCT Filed: May 20, 2019

(86) PCT No.: PCT/US2019/033036

§ 371 (c)(1),
(2) Date: Nov. 18, 2020

(87) PCT Pub. No.: WO2019/226506

PCT Pub. Date: Nov. 28, 2019

(65) Prior Publication Data

US 2021/0204867 A1 Jul. 8, 2021

Related U.S. Application Data

(60) Provisional application No. 62/674,903, filed on May 22, 2018.

(51) Int. Cl.
A61B 5/00 (2006.01)
A61B 5/0205 (2006.01)
(Continued)

(52) U.S. Cl.
CPC ............ A61B 5/486 (2013.01); A61B 5/0205 (2013.01); A61B 5/224 (2013.01); A61B 5/33 (2021.01);
(Continued)

(58) Field of Classification Search
CPC ............ A63B 24/0062; A63B 24/0602; A61B 5/7455; A61B 5/742; A61B 5/7405;
(Continued)

(56) References Cited

U.S. PATENT DOCUMENTS 9,956,470 B2 5/2018 Bleich et al.
2005/0124906 A1* 6/2005 Childre ................ A61B 5/0816
600/529

(Continued)

FOREIGN PATENT DOCUMENTS

EP 3202320 A1 8/2017
EP 19807392.6 2/2022
(Continued)

OTHER PUBLICATIONS

India Examination Report issued by the India Patent Office on Aug. 30, 2022, for India Patent Application No. 202047054511.
(Continued)

*Primary Examiner* — Amanda L Steinberg
(74) *Attorney, Agent, or Firm* — Ryan, Mason & Lewis, LLP

(57) ABSTRACT

A method includes monitoring first and second sets of physiologic parameters from at least one site on a subject utilizing at least one sensing device, identifying first and second events related to the first and second sets of physiologic parameters, generating first and second timestamps for the first and second events, determining a timing for providing feedback to the subject relative to the first timestamp and the second timestamp to adjust one or more characteristics of the subject during an activity, and providing one or more feedback signals to the subject in accordance with the determined timing utilizing at least one stimulating device. Adjusting one or more characteristics of the subject during the activity may include enhancing cardio-pulmonary performance of the subject during the activity, providing biomechanical enhancement of movement of at least a portion of the subject during the activity.

29 Claims, 12 Drawing Sheets

(51) Int. Cl.

| | |
|---|---|
| *A61B 5/08* | (2006.01) |
| *A61B 5/11* | (2006.01) |
| *A61B 5/22* | (2006.01) |
| *A61B 5/33* | (2021.01) |
| *A63B 24/00* | (2006.01) |

(52) U.S. Cl.
CPC .............. *A61B 5/08* (2013.01); *A61B 5/1101* (2013.01); *A61B 5/1107* (2013.01); *A61B 5/6833* (2013.01); *A61B 5/7405* (2013.01); *A61B 5/742* (2013.01); *A61B 5/7455* (2013.01); *A63B 24/0062* (2013.01)

(58) Field of Classification Search
CPC ......... A61B 5/6833; A61B 5/486; A61B 5/08; A61B 5/0205; A61B 5/224; A61B 5/1101; A61B 5/1107
See application file for complete search history.

(56) References Cited

U.S. PATENT DOCUMENTS

| | | | | |
|---|---|---|---|---|
| 2006/0040793 | A1 | 2/2006 | Martens | |
| 2011/0082511 | A1* | 4/2011 | Aarts | A63B 71/0686 |
| | | | | 607/11 |
| 2011/0307821 | A1 | 12/2011 | Martens | |
| 2013/0171599 | A1* | 7/2013 | Bleich | A63B 24/0062 |
| | | | | 434/247 |
| 2013/0212168 | A1 | 8/2013 | Bonasera et al. | |
| 2013/0303828 | A1 | 11/2013 | Hargrove | |
| 2014/0172040 | A1 | 6/2014 | Bauer | |
| 2014/0195023 | A1 | 7/2014 | Statham et al. | |
| 2014/0275857 | A1 | 9/2014 | Toth et al. | |
| 2015/0335288 | A1* | 11/2015 | Toth | A61B 5/6833 |
| | | | | 600/391 |
| 2015/0351690 | A1 | 12/2015 | Toth et al. | |
| 2016/0073874 | A1 | 3/2016 | Tsai et al. | |
| 2016/0206225 | A1* | 7/2016 | Todorov | A61B 5/222 |
| 2016/0310073 | A1 | 10/2016 | Kusik et al. | |
| 2017/0231490 | A1 | 8/2017 | Toth et al. | |
| 2018/0296157 | A1* | 10/2018 | Bleich | A61B 7/00 |
| 2020/0061378 | A1* | 2/2020 | Ganguly | A61B 5/7275 |

FOREIGN PATENT DOCUMENTS

| | | |
|---|---|---|
| WO | 2013070545 A1 | 5/2013 |
| WO | 2016019250 A1 | 2/2016 |
| WO | 2017066121 A1 | 4/2017 |
| WO | 2017096224 A1 | 6/2017 |
| WO | 2017190049 A1 | 11/2017 |
| WO | PCT/US2019/033036 | 8/2019 |

OTHER PUBLICATIONS

First Office Action in Chinese Application No. 201980034112.X, Jan. 21, 2024, 20 pages.

* cited by examiner

MONITORING PHYSIOLOGIC PARAMETERS FOR TIMING FEEDBACK TO ENHANCE PERFORMANCE OF A SUBJECT DURING AN ACTIVITY

TECHNICAL FIELD

The present disclosure relates to the field of physiologic monitoring and, more particularly, to devices and systems for monitoring physiologic parameters of a subject.

BACKGROUND

Physiologic monitoring is performed for a range of purposes. Existing technologies, however, are not without shortcomings.

There is a need to measure physiologic parameters of subjects reliably, simply, and without cables. As the proliferation of mobile and remote medicine increases, simplified and unobtrusive means for monitoring the physiologic parameters of a patient become more important.

SUMMARY

One illustrative, non-limiting objective of this disclosure is to provide systems, devices, methods, and kits for monitoring and management of physiologic parameters of a subject. Another illustrative, non-limiting objective is to provide a simplified system for monitoring subjects. Another illustrative, non-limiting objective is to provide comfortable long term wearable systems for monitoring subjects. Yet another illustrative, non-limiting objective is to provide systems for facilitating stimulation of a subject based on monitored physiologic parameters of the subject.

The above illustrative, non-limiting objectives are wholly or partially met by devices, systems, and methods according to the appended claims in accordance with the present disclosure. Features and aspects are set forth in the appended claims, in the following description, and in the annexed drawings in accordance with the present disclosure.

In one embodiment, an apparatus comprises a processor and a memory coupled to the processor, the processor being configured: to monitor a first set of one or more physiologic parameters and a second set of one or more physiologic parameters from at least one site on a subject utilizing at least one sensing device; to identify a first event related to the first set of one or more physiologic parameters and a second event related to the second set of one or more physiologic parameters; to generate a first timestamp for the first event and a second timestamp for the second event; to determine a timing for providing feedback to the subject relative to the first timestamp and the second timestamp to adjust one or more characteristics of the subject during an activity; and to provide one or more feedback signals to the subject in accordance with the determined timing utilizing at least one stimulating device.

Adjusting one or more characteristics of the subject during the activity may comprise at least one of enhancing cardio-pulmonary performance of the subject during the activity and providing biomechanical enhancement of movement of at least a portion of the subject during the activity.

The at least one sensing device and the at least one stimulating device may be the same.

The at least one sensing device may comprise a first sensing device attached to the subject at a first site and at least a second sensing device attached to the subject at a second site. The first set of physiologic parameters may be monitored at the first site utilizing the first sensing device and the second set of physiologic parameters may be monitored at the second site utilizing the second sensing device. The first site and the second site may be co-located on the subject. The first site may be located on an appendage, an arm, a hand, a leg, a foot, a thigh, a knee, a calf, an ankle, a bicep, an elbow, a forearm, a wrist, an abdomen, or a pelvis of the subject. The second site may be located on a torso, a rib cage, an abdomen, a neck, a head, an ear, under an arm, or on an appendage of the subject. At least one of the first site and the second site may be on at least one machine interfaced with the subject.

The first set of one or more physiologic parameters may comprise at least one of one or more kinematic and one or more myographic signals from the first site on the subject. The second set of one or more physiologic parameters may comprise at least one of one or more cardiologic and one or more respiratory signals from the second site on the subject. The first event may correspond to at least one of: one or more muscle activity levels; onset of one or more muscle contractions; relaxation of one or more muscles; peak contraction of one or more muscles; fatigue of one or more muscles; peak force generation by one or more muscles; peak myographic activity of one or more muscles; peak high frequency myographic activity of one or more muscles; peak fast twitch activity of one or more muscles; and peak slow twitch activity of one or more muscles. The first event may also or alternatively correspond to one or more kinematic and kinetic movements, the one or more kinematic and kinetic movements comprising one or more of: a peak horizontal acceleration; a peak horizontal velocity; a minimum vertical acceleration; a minimum vertical velocity; an apex of an arc; a base of an arc; an impact; a directional impact; and a free fall condition.

The monitoring may be performed while the subject performs a repetitive task. The repetitive task may comprise one of running, walking, cycling, lifting a weight, jumping, squatting, sit-ups, crunches, head movement, rowing, swimming, swinging an implement, and stair climbing.

Determining the timing for providing feedback to the subject relative to the first timestamp and the second timestamp may be based at least in part on one or more environmental factors.

Determining the timing for providing feedback to the subject relative to the first timestamp and the second timestamp may be based at least in part on one or more task-related factors for a repetitive task being performed by the subject.

Determining the timing for providing feedback to the subject relative to the first timestamp and the second timestamp may be based at least in part on one or more fatigue factors of the subject.

Determining the timing for providing feedback to the subject relative to the first timestamp and the second timestamp may comprise: performing a training procedure comprising applying stimulus to the subject utilizing the at least one stimulating device and monitoring one or more physiologic parameters of the subject to determine one or more changes in at least one cardiologic performance metric; and utilizing the determined one or more changes in the at least one cardiologic performance metric to determine an optimal timing for providing the feedback to the subject relative to the first timestamp and the second timestamp.

The subject may be performing a repetitive task comprising a plurality of cycles, and the processor may be configured to perform the monitoring during two or more of the plurality of cycles so as to perform time averaged optimization for providing the feedback to the subject in response to first timestamps and second timestamps associated with first events and second events in each of the two or more cycles.

The subject may be performing a repetitive task comprising a plurality of cycles, and the processor may be configured to perform the monitoring during a first one of the plurality of cycles and to provide the feedback to the subject in a second one of the plurality of cycles subsequent to the first cycle.

The subject may be performing a task comprising two or more activities during the monitoring, and determining the timing for providing the feedback relative to the first timestamp and the second timestamp may comprise coordinating the timing of the feedback for one or more designated activities within the task.

The feedback may comprise at least one of an electrical stimulus, a vibratory stimulus, an auditory stimulus, and a visual stimulus.

The processor may be further configured: to apply a stimulus to two or more locations on the subject utilizing the at least one stimulating device; to monitor a response of the subject to the stimulus provided at each of the two or more locations utilizing the at least one sensing device; to determine reflex times of the subject for stimulus applied to each of the two or more locations utilizing the monitored response; and to select at least a given one of the two or more locations for providing the one or more feedback signals to the subject based on the determined reflex times.

The processor may be configured to adjust an intensity of the one or more feedback signals provided to the subject to achieve a desired cardio-pulmonary performance enhancement level.

The processor may be configured to calculate one or more reflexes of the subject by monitoring the subject response relative to a timing of providing the one or more feedback signals to the subject to determine when the subject adjusts movement related to a task in response to the one or more feedback signals. The processor may be further configured to monitor one or more changes in reflex response time of the subject and to adjust timing of providing the one or more feedback signals to the subject based on the one or more changes in the reflex response time of the subject.

In another embodiment, a method comprises monitoring a first set of one or more physiologic parameters and a second set of one or more physiologic parameters from at least one site on a subject utilizing at least one sensing device, identifying a first event related to the first set of one or more physiologic parameters and a second event related to the second set of one or more physiologic parameters, generating a first timestamp for the first event and a second timestamp for the second event, determining a timing for providing feedback to the subject relative to the first timestamp and the second timestamp to adjust one or more characteristics of the subject during an activity, and providing one or more feedback signals to the subject in accordance with the determined timing utilizing at least one stimulating device.

Adjusting one or more characteristics of the subject during the activity may comprise at least one of enhancing cardio-pulmonary performance of the subject during the activity and providing biomechanical enhancement of movement of at least a portion of the subject during the activity.

In another embodiment, a computer program product comprises a non-transitory processor-readable storage medium having stored therein executable program code which, when executed, causes at least one processing device: to monitor a first set of one or more physiologic parameters and a second set of one or more physiologic parameters from at least one site on a subject utilizing at least one sensing device; to identify a first event related to the first set of one or more physiologic parameters and a second event related to the second set of one or more physiologic parameters; to generate a first timestamp for the first event and a second timestamp for the second event; to determine a timing for providing feedback to the subject relative to the first timestamp and the second timestamp to adjust one or more characteristics of the subject during an activity; and to provide one or more feedback signals to the subject in accordance with the determined timing utilizing at least one stimulating device.

Adjusting one or more characteristics of the subject during the activity may comprise at least one of enhancing cardio-pulmonary performance of the subject during the activity and providing biomechanical enhancement of movement of at least a portion of the subject during the activity.

BRIEF DESCRIPTION OF THE DRAWINGS

Several aspects of the disclosure can be better understood with reference to the following drawings. In the drawings, like reference numerals designate corresponding parts throughout the several views.

DETAILED DESCRIPTION

Figure 1:
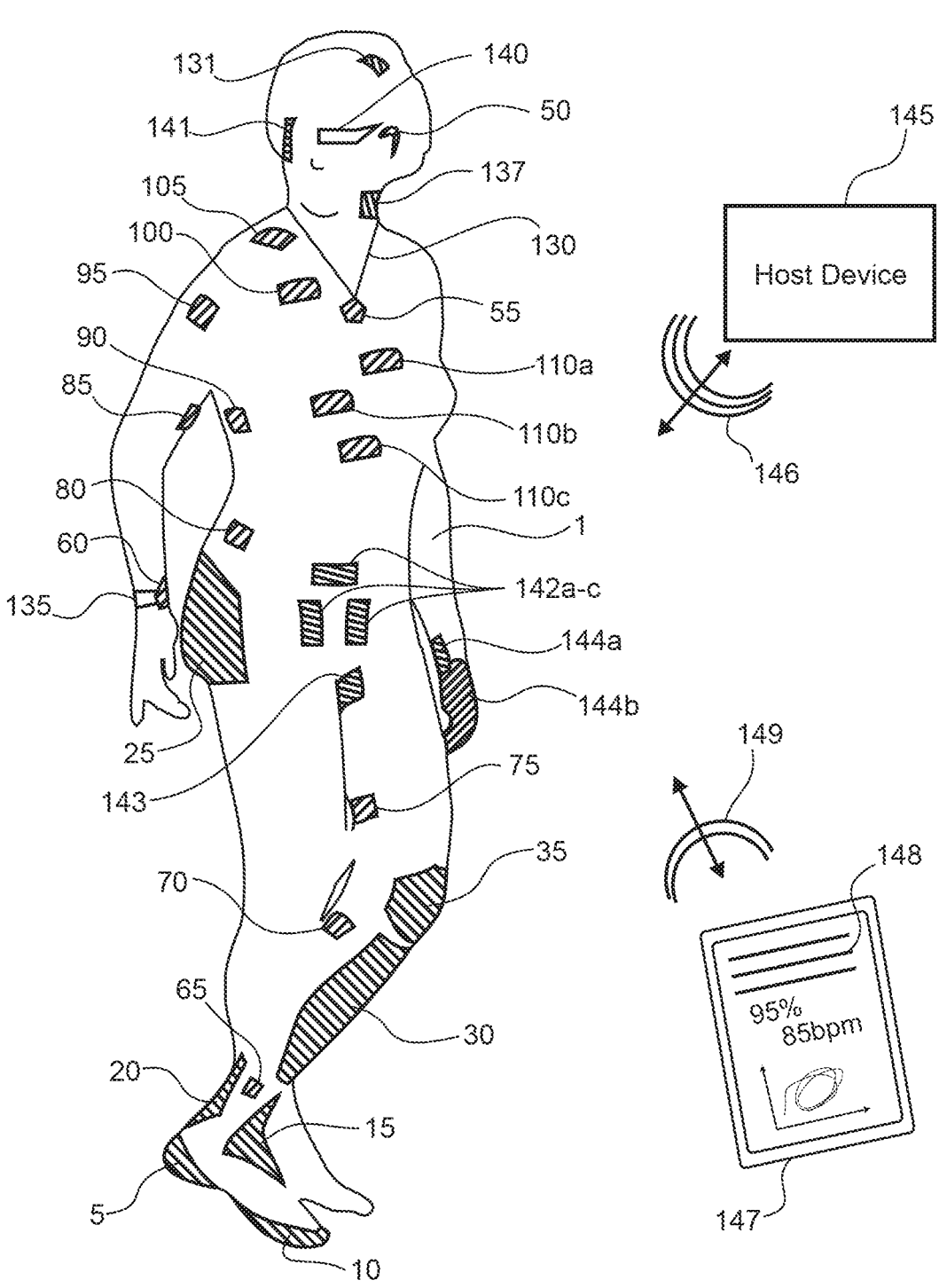
FIG. 1 illustrates aspects of a modular physiologic monitoring system, according to an embodiment of the invention.

Particular embodiments of the present disclosure are described herein below with reference to the accompanying drawings; however, the disclosed embodiments are merely examples of the disclosure and may be embodied in various forms. Therefore, specific structural and functional details disclosed herein are not to be interpreted as limiting, but merely as a basis for the claims and as a representative basis for teaching one skilled in the art to variously employ the present disclosure in virtually any appropriately detailed structure. Like reference numerals may refer to similar or identical elements throughout the description of the figures.

A modular physiologic monitoring system in accordance with the present disclosure for assessing one or more physiologic parameters of a subject (e.g., a human subject, a patient, an athlete, a trainer, an animal, such as equine, canine, porcine, bovine, etc.) may include one or more patches, each patch adapted for attachment to the body of the subject (e.g., attachable to the skin thereof, reversibly attachable, adhesively attachable, with a disposable interface and a reusable module, etc.). In aspects, the physiologic monitoring system may include one or more modules, and each module may include a power source (e.g., a battery, a rechargeable battery, an energy harvesting transducer, microcircuit, and an energy reservoir, a thermal gradient harvesting transducer, a kinetic energy harvesting transducer, a radio frequency energy harvesting transducer, a fuel cell, a biofuel cell, etc.), signal conditioning circuitry, communication circuitry, one or more sensors, or the like, configured to generate one or more signals (e.g., physiologic and/or physical signals), stimulus, etc.

One or more of the patches may include one or more interconnects, configured and dimensioned so as to couple with one or more of the modules, said modules including a complimentary interconnect configured and dimensioned to couple with the corresponding patch. The patch may include a bioadhesive interface for attachment to the subject, the module retainable against the subject via interconnection with the patch.

In aspects, the patch may be configured so as to be single use (e.g., disposable). The patch may include a thin, breathable, stretchable laminate. In aspects, the laminate may include a substrate, a bioadhesive, one or more sensing or stimulating elements in accordance with the present disclosure, and one or more interconnects for coupling one or more of the sensing elements with a corresponding module.

In aspects, to retain a high degree of comfort and long term wear-ability of the patch on a subject, to limit interference with normal body function, to limit interference with joint movement, or the like, the patch may be sufficiently thin and frail, such that it may not substantially retain a predetermined shape while free standing. Such a definition is described in further detail below. The patch may be provided with a temporary stiffening film to retain the shape thereof prior to placement of the patch onto the body of a subject. Once adhered to the subject, the temporary stiffening film may be removed from the patch. While the patch is adhered to the subject, the shape and functionality of the patch may be substantially retained. Upon removal of the patch from the subject, the, now freestanding patch is sufficiently frail such that the patch can no longer substantially retain the predetermined shape (e.g., sufficiently frail such that the patch will not survive in a free standing state). In aspects, stretch applied to the patch while removing the patch from the subject may result in snap back once the patch is in a freestanding state that renders such a patch to crumple into a ball and no longer function.

In aspects, the patch may include a film (e.g., a substrate), with sufficiently high tear strength, such that, as the patch is peeled from the skin of a subject, the patch does not tear. In aspects, the ratio between the tear strength of the patch and the peel adhesion strength of the patch to skin (e.g., tear strength: peel adhesion strength), is greater than 8:1, greater than 4:1, greater than 2:1, or the like. Such a configuration may be advantageous so as to ensure the patch may be easily and reliably removed from the subject after use without tearing.

In aspects, the patch may include a bioadhesive with peel tack to mammalian skin of greater than 0.02 Newtons per millimeter (N/mm), greater than 0.1 N/mm, greater than 0.25 N/mm, greater than 0.50 N/mm, greater than 0.75 N/mm, greater than 2 N/mm, or the like. Such peel tack may be approximately determined using an American Society for Testing and Materials (ASTM) standard test, ASTM D3330: Standard test method for peel adhesion of pressure-sensitive tape.

In aspects, the patch may exhibit a tear strength of greater than 0.5 N/mm, greater than 1 N/mm, greater than 2 N/mm, greater than 8 N/mm, or the like. Such tear strength may be approximately determined using an ASTM standard test, ASTM D624: Standard test method for tear strength of conventional vulcanized rubber and thermoplastic elastomers.

In aspects, the patch may be provided with a characteristic thickness of less than 50 micrometer ($\mu$m), less than 25 $\mu$m, less than 12 $\mu$m, less than 8 $\mu$m, less than 4 $\mu$m, or the like. Yet, in aspects, a balance between the thickness, stiffness, and tear strength may be obtained so as to maintain sufficiently high comfort levels for a subject, minimizing skin stresses during use (e.g., minimizing skin stretch related discomfort and extraneous signals as the body moves locally around the patch during use), minimizing impact on skin health, minimizing risk of rucking during use, and minimizing risk of maceration to the skin of a subject, while limiting risk of tearing of the patch during removal from a subject, etc.

In aspects, the properties of the patch may be further altered so as to balance the hydration levels of one or more hydrophilic or amphiphilic components of the patch while attached to a subject. Such adjustment may be advantageous to prevent over hydration or drying of an ionically conducting component of the patch, to manage heat transfer coefficients within one or more elements of the patch, to manage salt retention into a reservoir in accordance with the present disclosure, and/or migration during exercise, to prevent pooling of exudates, sweat, or the like into a fluid measuring sensor incorporated into the patch or associated module, etc. In aspects, the patch or a rate determining component thereof may be configured with a moisture vapor transmission rate of between 200 grams per meter squared per 24 hours (g/m²/24 hrs) and 20,000 g/m²/24 hrs, between 500 g/m²/24 hrs and 12,000 g/m²/24 hrs, between 2,000 g/m²/24 hrs and 8,000 g/m²/24 hrs, or the like.

Such a configuration may be advantageous for providing a comfortable wearable physiologic monitor for a subject, while reducing material waste and/or cost of goods, preventing contamination or disease spread through uncontrolled re-use, and the like.

In aspects, one or more patches and/or modules may be configured for electrically conducting interconnection, inductively coupled interconnection, capacitively coupled interconnection, with each other. In the case of an electrically conducting interconnect, each patch and module interconnect may include complimentary electrically conducting connectors, configured and dimensioned so as to mate together upon attachment. In the case of an inductively or capacitively coupled interconnect, the patch and module may include complimentary coils or electrodes configured and dimensioned so as to mate together upon attachment.

Each patch or patch-module pair may be configured as a sensing device to monitor one or more local physiologic and/or physical parameters of the attached subject (e.g., local to the site of attachment, etc.), local environment, combinations thereof, or the like, and to relay such information in the form of signals to a host device (e.g., via a wireless connection, via a body area network connection, or the like), one or more patches or modules on the subject, or the like. Each patch and/or patch-module pair may also or alternatively be configured as a stimulating device to apply a stimulus to the subject in response to signaling from the host device, the signaling being based on analysis of the physiologic and/or physical parameters of the subject measured by the sensing device(s).

In aspects, the host device may be configured to coordinate information exchange to/from each module and/or patch, and to generate one or more physiologic signals, physical signals, environmental signals, kinetic signals, diagnostic signals, alerts, reports, recommendation signals, commands, combinations thereof, or the like for the subject, a user, a network, an electronic health record (EHR), a database (e.g., as part of a data management center, an EHR, a social network, etc.), a processor, combinations thereof, or the like.

In aspects, a system in accordance with the present disclosure may include a plurality of substantially similar modules (e.g., generally interchangeable modules, but with unique identifiers), for coupling with a plurality of patches, each patch, optionally different from the other patches in the system (e.g., potentially including alternative sensors, sensor types, sensor configurations, electrodes, electrode configurations, etc.). Each patch may include an interconnect suitable for attachment to an associated module. Upon attachment of a module to a corresponding patch, the module may validate the type and operation of the patch to which it has been mated. In aspects, the module may then initiate monitoring operations on the subject via the attached patch, communicate with one or more patches on the subject, a hub, etc. The data collection from each module may be coordinated through one or more modules and/or with a host device in accordance with the present disclosure. The modules may report a time stamp along with the data in order to synchronize data collection across multiple patch-module pairs on the subject, between subjects, etc. Thus, if a module is to be replaced, a hot swappable replacement (e.g., replacement during a monitoring procedure) can be carried out easily by the subject, a caregiver, practitioner, etc. during the monitoring process. Such a configuration may be advantageous for performing redundant, continuous monitoring of a subject, and/or to obtain spatially relevant information from a plurality of locations on the subject during use.

In aspects, the modules and/or patches may include corresponding interconnects for coupling with each other during use. The interconnects may include one or more connectors, configured such that the modules and patches may only couple in a single unique orientation with respect to each other. In aspects, the modules may be color coded by function. A temporary stiffening element attached to a patch may include instructions, corresponding color coding, etc. so as to assist a user or subject with simplifying the process of monitoring.

In addition to physiologic monitoring, one or more patches and/or modules may be used to provide a stimulus to the subject, as will be described in further detail below.

A modular physiologic monitoring system, in some embodiments, includes one or more sensing devices, which may be placed or attached to one or more sites on the subject. Alternatively or additionally, one or more sensing devices may be placed "off" the subject, such as one or more sensors (e.g., cameras, acoustic sensors, etc.) that are not physically attached to the subject. The sensing devices are utilized to establish whether or not an event is occurring and to determine one or more characteristics of the event by monitoring and measuring physiologic parameters of the subject. The determination of whether an event has occurred or is occurring may be made by a device that is at least partially external and physically distinct from the one or more sensing devices, such as a host device in wired or wireless communication with the sensing devices as described below with respect to FIG. 1. The modular physiologic monitoring system includes one or more stimulating devices, which again may be any combination of devices that are attached to the subject or placed "off" the subject, to apply a stimulus to the subject in response to a detected event. Various types of stimulus may be applied, including but not limited to stimulating via thermal input, vibration input, mechanical input, a compression or the like with an electrical input, etc.

The sensing devices of a modular physiologic monitoring system, such as patch-module pairs described below with respect to FIG. 1, may be used to monitor one or more physiologic functions or parameters of a subject, as will be described in further detail below. The sensing devices of the modular physiologic monitoring system, or a host device configured to receive data or measurements from the sensing devices, may be utilized to monitor for one or more events (e.g., through analysis of signals measured by the sensing devices, from metrics derived from the signals, etc.). The stimulating devices of the modular physiologic monitoring system may be configured to deliver one or more stimuli (e.g., electrical, vibrational, acoustic, visual, etc.) to the subject. The stimulating devices may receive a signal from one or more of the sensing devices or a host device, and provide the stimulation in response to the received signal.

FIG. 1 shows aspects of a modular physiologic monitoring system in accordance with the present disclosure. In FIG. 1, a subject 1 is shown with a number of patches and/or patch-module pairs each in accordance with the present disclosure attached thereto at sites described below, a host device 145 in accordance with the present disclosure, a feedback/user device 147 in accordance with the present disclosure displaying some data 148 based upon signals obtained from the subject 1, and one or more feedback devices 135, 140, in accordance with the present disclosure configured to convey to the subject 1 one or more aspects of the signals or information gleaned therefrom. In some embodiments, the feedback devices 135, 140 may also or alternatively function as stimulating devices. The host device 145, the user device 147, the patches and/or patch-module pairs, and/or the feedback devices 135, 140 may be configured for wireless communication 146, 149 during a monitoring session.

In aspects, a patch-module pair may be adapted for placement almost anywhere on the body of a subject 1. As shown in FIG. 1, some sites may include attachment to the cranium or forehead 131, the temple, the ear or behind the ear 50, the neck, the front, side, or back of the neck 137, a shoulder 105, a chest region with minimal muscle mass 100, integrated into a piece of ornamental jewelry 55 (may be a host, a hub, a feedback device, etc.), arrangement on the torso 110a-c, arrangement on the abdomen 80 for monitoring movement or breathing, below the rib cage 90 for monitoring respiration (generally on the right side of the body to substantially reduce ECG influences on the measurements), on a muscle such as a bicep 85, on a wrist 135 or in combination with a wearable computing device 60 on the wrist (e.g., a smart watch, a fitness band, etc.), on a buttocks 25, on a thigh 75, on a calf muscle 70, on a knee 35 particularly for proprioception based studies and impact studies, on a shin 30 primarily for impact studies, on an ankle 65, over an Achilles tendon 20, on the front or top of the foot 15, on a heel 5, or around the bottom of a foot or toes 10. Other sites for placement of such devices are envisioned. Selection of the monitoring and/or stimulating sites is generally determined based upon the intended application of the patch-module pairs described herein.

Additional placement sites on the abdomen, perineal region 142a-c, genitals, urogenital triangle, anal triangle, sacral region, inner thigh 143, or the like may be advantageous in the assessment of autonomic neural function of a subject. Such placements regions may be advantageous for assessment of parasympathetic nervous system (PNS) activity, somatosensory function, assessment of sympathetic nervous system (SNS) functionality, etc.

Placement sites on the wrist 144a, hand 144b or the like may advantageous for interacting with a subject, such as via performing a stress test, performing a thermal stress test, performing a tactile stress test, monitoring outflow, afferent traffic, efferent traffic, etc.

Placement sites on the nipples, areola, lips, labia, clitoris, penis, the anal sphincter, levator ani muscle, over the ischiocavernous muscle, deep transverse perineal muscle, labium minus, labium majus, one or more nerves near the surface thereof, posterior scrotal nerves, perineal membrane, perineal nerves, superficial transverse perineal nerves, dorsal nerves, inferior rectal nerves, etc. may be advantageous for assessment of autonomic neural ablation procedures, autonomic neural modulation procedures, assessment of the PNS of a subject, assessment of sexual dysfunction of a subject, etc.

Placement sites on the face 141, over ocular muscles, near the eye, over a facial muscle (e.g., a nasalis, temporalis, zygonaticus minor/major, orbicularis oculi, occipitofrontalis), near a nasal canal, over a facial bone (e.g., frontal process, zygomatic bone/surface, zygomaticofacial foreman, malar bone, nasal bone, frontal bone, maxilla, temporal bone, occipital bone, etc.), may be advantageous to assess ocular function, salivary function, sinus function, interaction with the lips, interaction with one or more nerves of the PNS (e.g., interacting with the vagus nerve within, on, and/or near the ear of the subject), etc.

In aspects, a system in accordance with the present disclosure may be configured to monitor one or more physiologic parameters of the subject 1 before, during, and/or after one or more of, a stress test, consumption of a medication, exercise, a rehabilitation session, a massage, driving, a movie, an amusement park ride, sleep, intercourse, a surgical, interventional, or non-invasive procedure, a neural remodeling procedure, a denervation procedure, a sympathectomy, a neural ablation, a peripheral nerve ablation, a radio-surgical procedure, an interventional procedure, a cardiac repair, administration of an analgesic, a combination thereof, or the like. In aspects, a system in accordance with the present disclosure may be configured to monitor one or more aspects of an autonomic neural response to a procedure, confirm completion of the procedure, select candidates for a procedure, follow up on a subject after having received a procedure, assess the durability of a procedure, or the like (e.g., such as wherein the procedure is a renal denervation procedure, a carotid body denervation procedure, a hepatic artery denervation procedure, a LUTs treatment, a bladder denervation procedure, a urethral treatment, a prostate ablation, a prostate nerve denervation procedure, a cancer treatment, a pain block, a neural block, a bronchial denervation procedure, a carotid sinus neuromodulation procedure, implantation of a neuromodulation device, tuning of a neuromodulation device, etc.).

Additional details regarding modular physiologic monitoring systems, kits and methods are further described in PCT application serial no. PCT/US2014/041339, published as WO 2014/197822 and titled "Modular Physiologic Monitoring Systems, Kits, and Methods," PCT application serial no. PCT/US2015/043123, published as WO 2016/019250 and titled "Modular Physiologic Monitoring Systems, Kits, and Methods," and PCT application serial no. PCT/US2017/030186, published as WO 2017/190049 and titled "Monitoring and Management of Physiologic Parameters of a Subject," the disclosures of which are incorporated by reference herein in their entirety.

Various embodiments are described below with respect to utilizing a modular physiologic monitoring system for monitoring cardiac output, and utilizing information related to cardiac output to coordinate periodic compression and relaxation of microvascular blood vessel networks. Such techniques provide various advantages, such as achieving significant afterload reduction, which lessens the workload of the heart since comparable blood flow is achieved with the same or less cardiac work. These and other advantages will be described in further detail below.

In some embodiments, modular physiologic monitoring systems may include sensing and stimulating devices that are physically distinct, such as sensing and stimulating devices that are physically attached to a subject at varying locations. For example, the sensing and stimulating devices may include different ones of the patch-module pairs described above with respect to FIG. 1. In other embodiments, one or more devices may provide both monitoring and stimulating functionality. For example, one or more of the patch-module pairs described above with respect to FIG. 1 may be configured to function as both a sensing device and a stimulating device. It is to be appreciated, however, that embodiments are not limited solely to use with the patch-module pairs of FIG. 1 as sensing and stimulating devices. Various other types of sensing and stimulating devices may be utilized, including but not limited to sensors that are "off-body" with respect to subject 1.

The sensing and/or stimulating devices of a modular physiologic monitoring system may be configured for radio frequency (RF) or other wireless and/or wired connection with one another and/or a host device. Such RF or other connection may be used to transmit or receive feedback parameters or other signaling between the sensing and stimulating devices. The feedback, for example, may be provided based on measurements of physiologic parameters that are obtained using the sensing devices to determine when events related to cardiac output are occurring. Various thresholds for stimulation that are applied by the stimulating devices may, in some embodiments, be determined based on such feedback. Thresholds may relate to the amplitude or frequency of electric or other stimulation. Thresholds may also be related to whether to initiate stimulation by the stimulating devices based on the feedback.

During and/or after stimulus is applied with the stimulating devices, the sensing devices may monitor the physiologic response of the subject. If stimulation is successful in achieving a desired response, the stimulation may be discontinued. Otherwise, the type, timing, etc. of stimulation may be adjusted.

In some embodiments, a user of the modular physiologic monitoring system may set preferences for the stimulus type, level, and/or otherwise personalize the sensation during a setup period or at any point during use of the modular physiologic monitoring system. The user of the modular physiologic monitoring system may be the subject being monitored and stimulated by the sensing devices and stimulating devices, or a doctor, nurse, physical therapist, medical assistant, caregiver, etc. of the subject being monitored and stimulated. The user may also have the option to disconnect or shut down the modular physiologic monitoring system at any time, such as via operation of a switch, pressure sensation, voice operated instruction, etc.

Stimulus or feedback which may be provided via one or more stimulating devices in a modular physiologic monitoring system may be in various forms, including physical stimulus (e.g., electrical, thermal, vibrational, pressure, stroking, a combination thereof, or the like), optical stimulus, acoustic stimulus, etc.

Physical stimulus may be provided in the form of negative feedback, such as in a brief electric shock or impulse as described above. Data or knowledge from waveforms applied in conducted electrical weapons (CEWs), such as in electroshock devices, may be utilized to avoid painful stimulus. Physical stimulus may also be provided in the form of positive feedback, such as in evoking pleasurable sensations by combining non-painful electrical stimulus with pleasant sounds, music, lighting, smells, etc. Physical stimulus is not limited solely to electrical shock or impulses. In other embodiments, physical stimulus may be provided by adjusting temperature or other stimuli, such as in providing a burst of cool or warm air, a burst of mist, vibration, tension, stretch, pressure, etc.

Feedback provided via physical stimulus as well as other stimulus described herein may be synchronized with, initiated by or otherwise coordinated or controlled in conjunction with one or more monitoring devices (e.g., a host device, one or more sensing devices, etc.). The monitoring devices may be connected to the stimulating devices physically (e.g., via one or more wires or other connectors), wirelessly (e.g., via radio or other wireless communication), etc. Physical stimulus may be applied to various regions of a subject, including but not limited to the wrist, soles of the feet, palms of the hands, nipples, forehead, ear, mastoid region, the skin of the subject, etc.

Optical stimulus may be provided via one or more stimulating devices. The optical stimulus may be positive or negative (e.g., by providing pleasant or unpleasant lighting or other visuals). Acoustic stimulus similarly may be provided via one or more stimulating devices, as positive or negative feedback (e.g., by providing pleasant or unpleasant sounds). Acoustic stimulus may take the form of spoken words, music, etc. Acoustic stimulus, in some embodiments may be provided via smart speakers or other electronic devices such as Amazon Echo®, Google Home®, etc. The stimulus itself may be provided so as to elicit a particular psychophysical or psychoacoustic effect in the subject, such as directing the subject to stop an action, to restart an action (such as breathing), to adjust an action (such as a timing between a step and a respiratory action, between a muscle contraction and a leg position, etc.).

As described above, the modular physiologic monitoring system may operate in a therapeutic mode, in that stimulation is provided when one or more cardiac parameters of a subject indicate some event (e.g., actual, imminent or predicted failure or worsening). The modular physiologic monitoring system, however, may also operate as or provide a type of cardiac "pacemaker" in other embodiments. In such embodiments, the modular physiologic monitoring system has the potential to reduce the frequency of cardiac events, or to possibly avoid certain cardiac events altogether. A modular physiologic monitoring system may provide functionality for timing and synchronizing periodic compression and relaxation of microvascular blood vessel networks with cardiac output. Such techniques may be utilized to respond to a type of failure event as indicated above. Alternatively or additionally, such techniques may be provided substantially continuously, so as to improve overall cardiac performance (e.g., blood flow) with the same or less cardiac work.

In some embodiments, a modular physiologic monitoring system may be configured to provide multi-modal stimuli to a subject. Multi-modal approaches use one or more forms of stimulation (e.g., thermal and electrical, mechanical and electrical, etc.) in order to mimic another stimulus to trick local nerves into responding in the same manner to the mimicked stimulus. In addition, in some embodiments multi-modal stimulus or input may be used to enhance a particular stimulus. For example, adding a mimicked electrical stimulus may enhance the effect of a thermal stimulus.

Modular physiologic monitoring systems may use pulses across space and time (e.g., frequency, pulse trains, relative amplitudes, etc.) to mimic vibration, comfort or discomfort, mild or greater pain, wet sensation, heat/cold, training neuroplasticity, taste (e.g., using a stimulating device placed in the mouth or on the tongue of a subject to mimic sour, sweet, salt, bitter or umami flavor), tension or stretching, sound or acoustics, sharp or dull pressure, light polarization (e.g., linear versus polar, the "Haidinger Brush"), light color or brightness, etc.

Stimulus amplification may also be provided by one or more modular physiologic monitoring systems using multi-modal input. Stimulus amplification represents a hybrid approach, wherein a first type of stimulus may be applied and a second, different type of stimulus provided to enhance the effect of the first type of stimulus. As an example, a first stimulus may be provided via a heating element, where the heating element is augmented by nearby electrodes or other stimulating devices that amplify and augment the heating stimulus using electrical mimicry in a pacing pattern. Electrical stimulus may also be used as a supplement or to mimic various other types of stimulus, including but not limited to vibration, heat, cold, etc. Different, possibly unique, stimulation patterns may be applied to the subject, with the central nervous system and peripheral nervous system interpreting such different or unique stimulation patterns as different stimulus modalities.

Another example of stimulus augmentation is sensing a "real" stimulus, measuring the stimulus, and constructing a proportional response by mimicry such as using electric pulsation. The real stimulus, such as sensing heat or cold from a Peltier device, may be measured by electrical-thermal conversion. This real stimulus may then be amplified using virtual mimicry, which may provide energy savings and the possibility of modifying virtual stimulus to modify the perception of the real stimulus.

In some embodiments, the stimulating devices in a modular physiologic monitoring system include an electrode array that attaches (e.g., via an adhesive or which is otherwise held in place) to a preferred body part. One or more of the stimulating devices may include a multiplicity of both sensing and stimulation electrodes, including different types of sensing and/or stimulation electrodes. The sensing electrodes on the stimulation devices, in some embodiments, may be distinct from the sensing devices in the modular physiologic monitoring system in that the sensing devices in the modular physiologic monitoring system may be used to measure physiologic parameters of the subject while the sensing electrodes on the stimulation devices in the modular physiologic monitoring system may be utilized to monitor the application of a stimulus to the subject.

A test stimulus may be initiated in a pattern in the electrode array, starting from application via one or a few of the stimulation electrodes and increasing in number over time to cover an entire or larger portion of the electrode array. The test stimulus may be used to determine the subject's response to the applied stimulation. Sensing electrodes on the stimulation devices may be used to monitor the application of the stimulus. The electrode array may also be used to record a desired output (e.g., physiologic parameters related to cardiac output). As such, one or more of the electrodes in the array may be configured so as to measure the local evoked response associated with the stimulus itself. Such an approach may be advantageous to confirm capture of the target nerves during use. By monitoring the neural response to the stimulus, the stimulus parameters including amplitude, duration, pulse number, etc. may be adjusted while ensuring that the target nerves are enlisted by the stimulus in use.

The test stimulus may migrate or be applied in a pattern to different electrodes at different locations in the electrode array. The response to the stimulus may be recorded or otherwise measured, using the sensing devices in the modular physiologic monitoring system and/or one or more of the sensing electrodes of the stimulating devices in the modular physiologic monitoring system. The response to the test stimulus may be recorded or analyzed to determine an optimal sensing or application site for the stimulus to achieve a desired effect or response in the subject. Thus, the test stimulus may be utilized to find optimal sensing (e.g., dermatome driver) location. This allows for powerful localization for optimal pacing or other application of stimulus, which may be individualized for different subjects.

A stimulating device applied to the subject via an adhesive (e.g., an adhesively applied stimulating device), may be in the form of a disposable or reusable unit, such as a patch and or patch-module or patch/hub pair as described above with respect to FIG. 1. An adhesively applied stimulating device, in some embodiments, includes a disposable interface configured so as to be thin, stretchable, able to conform to the skin of the subject, and sufficiently soft for comfortable wear. The disposable interface may be built from very thin, stretchable and/or breathable materials, such that the subject generally does not feel the device on his or her body.

The adhesively applied stimulating device also includes a means for interfacing with the subject through an adhesive interface and/or a window in the adhesive interface. Such means may include a plurality of electrodes that are coupled with a reusable component of the adhesively applied stimulating device and that are coupled to the body of the subject through the adhesive interface. The means may also or alternatively include: a vibrating actuator to provide vibration normal to and/or transverse to the surface of the skin on which the adhesively applied stimulating device is attached to the subject; a thermal device such as a Peltier device, a heating element, a cooling element, an RF heating circuit, an ultrasound source, etc.; a means for stroking the skin such as a shape memory actuator, an electroactive polymer actuator, etc.; a means for applying pressure to the skin such as a pneumatic actuator, a hydraulic actuator, etc.

Actuation means of the adhesively applied stimulating device may be applied over a small region of the applied area of the subject, such that the adhesive interface provides the biasing force necessary to counter the actuation of the actuation means against the skin of the subject.

Adhesively applied stimulating devices may be provided as two components—a disposable body interface and a reusable component. The disposable body interface may be applied so as to conform to the desired anatomy of the subject, and wrap around the body such that the reusable component may interface with the disposable component in a region that is open and free from a natural interface between the subject and another surface.

An adhesively applied stimulating device may also be a single component, rather than a two component or other multi-component arrangement. Such a device implemented as a single component may include an adhesive interface to the subject including two or more electrodes that are applied to the subject. Adhesively applied stimulating devices embodied as a single component provide potential advantages such as easier application to the body of the subject, but may come at a disadvantage with regards to one or more of breathability, conformity, access to challenging interfaces, etc. relative to two component or multi-component arrangements.

Figures 2, 3, 4, 5:
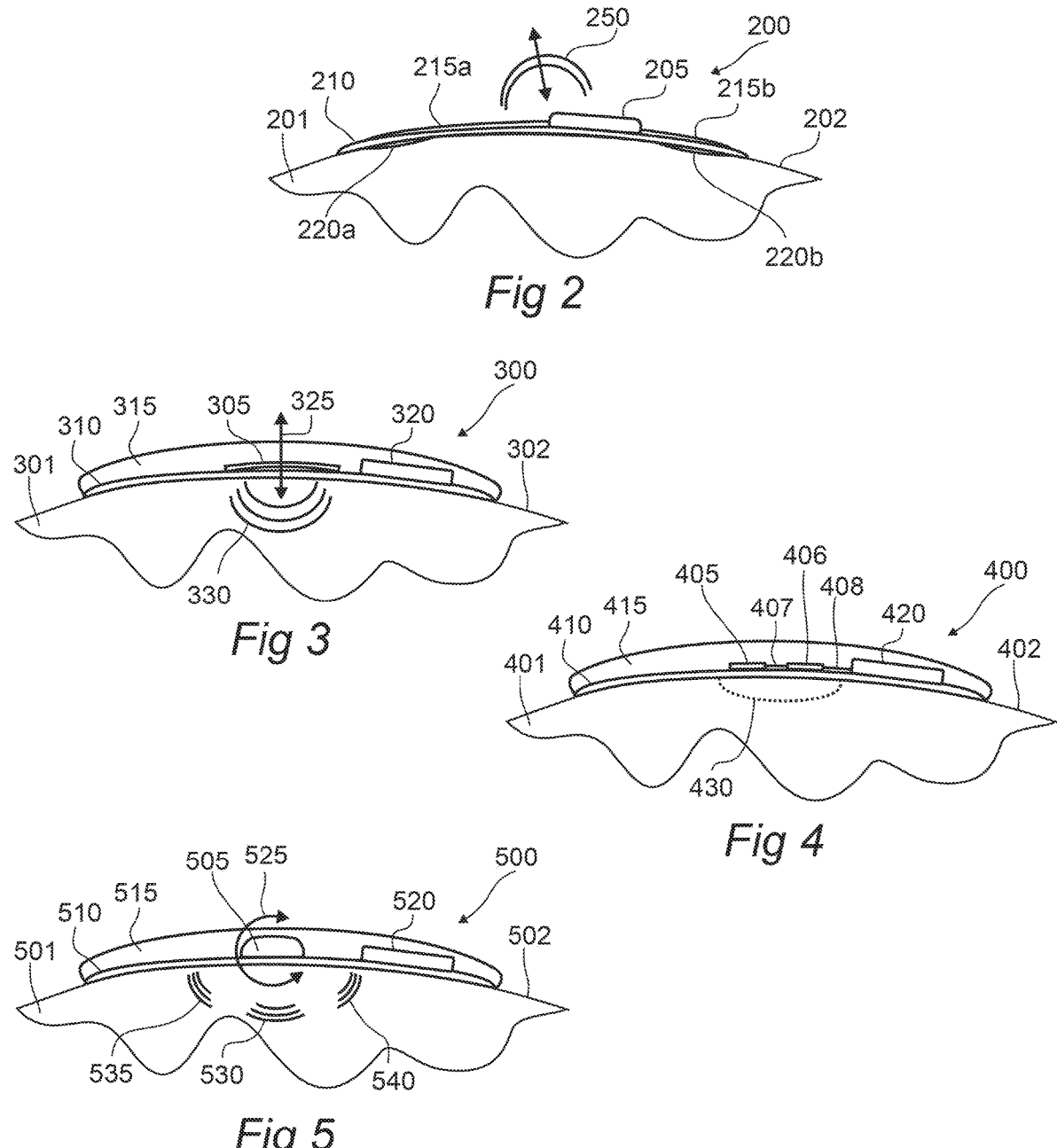
FIG. 2 illustrates an adhesively-applied stimulating device comprising a patch-module pair, according to an embodiment of the invention.
FIG. 3 illustrates a patch-module pair with vibratory stimulus means, according to an embodiment of the invention.
FIG. 4 illustrates a patch-module pair with thermal stimulus means, according to an embodiment of the invention.
FIG. 5 illustrates a patch-module pair with tactile stimulus means, according to an embodiment of the invention.

FIG. 2 illustrates an example of an adhesively applied stimulating device embodied as a patch-module pair 200. As shown, the patch-module pair 200, including module 205 coupled to patch 210, is applied to a skin surface 202 of a subject 201. It is to be appreciated that the patch-module pair 200 may function as a sensing device in addition to or instead of a stimulating device depending on the functionality of the electrodes 215a, 215b, 220a, 220b included in the patch 210. Electrodes 215a, 215b are outwardly facing (e.g., away from the skin surface 202 of the subject 201). Electrodes 220a, 220b interface with the skin surface 202 of the subject 201. One or more of the electrodes 215a, 215b, 220a, 220b may be used as sensors to sense physiologic parameters associated with the subject 201 and/or the ambient environment around the subject 201. One or more of the electrodes 215a, 215b, 220a, 220b may also or alternatively be configured to apply stimuli to the subject 201.

The patch-module pair 200 is in wireless communication 250 with one or more other devices in a modular physiologic monitoring system, such as one or more other stimulating devices, one or more sensing devices and/or a host device. Advantageously, patch 210 may be stretchy so as to maintain monitoring and/or application of stimuli to the subject 201 in light of movements, changes in shape or stretching along the skin surface 202 of the subject 201. The patch-module pair 200 is an example of a multi-component adhesively applied device, in that the patch-module pair 200 includes a low cost disposable patch 210 and a miniature reusable module 205. Such a configuration may be advantageous to provide a soft and comfortable sensing and/or stimulating device for a modular physiologic monitoring system.

As discussed above, various types of input or stimulus may be applied to a subject with a stimulating device. In some embodiments, the stimulus is in the form of electrical shock. For example, the skin-interfacing electrodes 220a, 220b of patch 210 may be configured to apply electrical energy to the subject 201. FIGS. 3-5 show examples of adhesively applied stimulating devices which utilize other means for applying other types of stimulus.

FIG. 3 illustrates a patch-module pair 300 configured to apply vibrational energy or stimulus 325 to the skin surface 302 of subject 301. The patch-module pair 300 includes an adhesive layer 310 (e.g., potentially forming part of a patch) and a module 315. The adhesive layer 310 secures the patch-module pair 300 to the skin surface 302 of the subject 301. The module 315 includes a transducer 305 configured to generate vibrational energy 325 for transfer 330 into the subject 301. The transducer 305 may be controlled and/or powered by an electronics unit 320 included in the module 315. In the non-limiting example shown, the transducer 305 may be piezoelectric material (e.g., a polymer, ceramic, etc.).

FIG. 4 illustrates a patch-module pair 400 for applying thermal energy or stimulus 430 to a subject 401. The patch-module pair 400 includes an adhesive layer 410 (e.g., potentially forming part of a patch) and a module 415. The adhesive layer 410 secures the patch-module pair 400 to the skin surface 402 of the subject 401. The module 415 includes one or more heater bands 405 or RF heating circuits, and thermocouples 406 coupled to an electronics unit 420 including a power source, a microcircuit, etc. via one or more electronic interconnects 407, 408.

FIG. 5 illustrates a patch-module pair 500 for applying a tactile input or stimulus 525 to a subject 501. The patch-module pair 500 includes an adhesive layer 510 (e.g., potentially forming part of a patch) and a module 515. The adhesive layer 510 secures the patch-module pair 500 to the skin surface 502 of the subject 501. The module 515 includes a transducer 505 configured to generate torsional energy 525 for transfer 530, 535, 540 into the subject 501. The transducer 505 may be controlled and/or powered by an electronics unit 520 included in the module 515. In the non-limiting example shown, the transducer 505 may be an electric motor with an eccentricity on the output shaft thereof. The transfer 530, 535, 540 of energy into the skin surface 502 of the subject 501 may induce a range of sensations (e.g., poking, rubbing, etc.) dependent upon the amplitude, frequency, duration, duty cycle, etc. of the transducer 505 as well as the physical configuration of the patch-module pair 500 and the choice of adhesive layer 510, if such a layer is used in the embodiment in question.

It is to be appreciated that the means described with respect to FIGS. 2-5 for applying stimulus to a subject are not limited to use solely in stimulating devices that utilize an adhesively applied form factor. Similar means may be utilized in other form factors described herein.

FIGS. 6a-e illustrate non-limiting examples of patch electrode layouts.

Figure 6A:
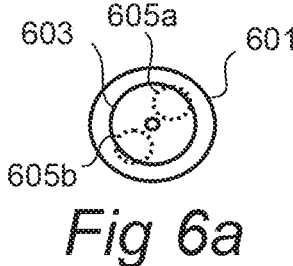
FIGS. 6a-6e illustrate electrode layouts, according to an embodiment of the invention.

FIG. 6a shows a patch 601 coupled to a module 603. The patch 601 includes a plurality of electrodes 605a, 605b for interfacing with a subject. The electrodes 605a, 605b are arranged in a very tight bipolar arrangement suitable for obtaining a bipolar electrical reading from the surface of a subject with a very small profile. In aspects, one or more of the electrodes 605a, 605b may include an electrode feature for enhancing the electrical coupling between the module 603 and the underlying tissues of a subject. In aspects, pressure applied to the top of an attached module 603 may be suitable for engaging such an electrode feature with the underlying tissue of the subject. Such an arrangement may be advantageous for providing an ultra-miniature heart-rate monitor, a pediatric heart-rate monitor, an EMG sensor for placement near a sexual organ, an electrophysiological monitor behind an ear, on a neck, etc., and/or to provide a stimulating device as described herein.

Figure 6B:
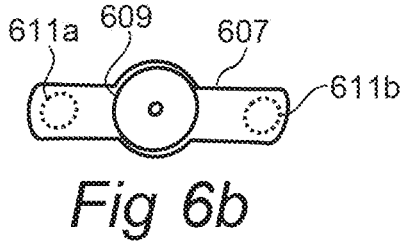

FIG. 6b shows a patch 607 coupled to a module 609. The patch 607 includes a bipolar electrode arrangement 611a, 611b for interfacing with a subject. Such an arrangement may be advantageous for monitoring heart rate, a signal channel ECG, respiration rate, etc. of a subject as part of a monitoring session, and/or to provide a stimulating device as described herein. A plurality of such patches 607 may be applied to a subject to simultaneously extract a higher level or spatially distributed electrical field over the body of the subject.

Figure 6C:
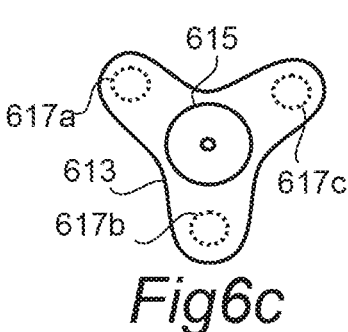

FIG. 6c shows a patch 613 coupled to a module 615. The patch 613 includes three electrodes 617a, 617b, 617c for interfacing with a subject. The electrodes 617a, 617b, 617c may be arranged so as to allow for multi-site capture of electrophysiological activity on the subject. Such an arrangement may be advantageous for generating a field vector in the vicinity of the patch 613, and/or for applying a stimulus to the subject.

Figure 6D:
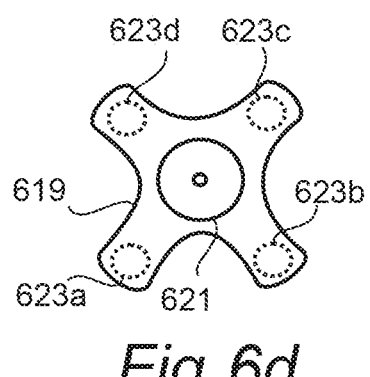

FIG. 6d shows a patch 619 coupled to a module 621 each in accordance with the present disclosure. The patch 619 includes a quadripolar electrode arrangement 623a, 623b, 623c, 623d for interfacing with a subject. The quadripolar electrodes 623a, 623b, 623c, 623d may be arranged so as to allow for multi-site capture of electrophysiological activity on the subject, and/or for applying stimuli to the subject. Such an arrangement may be advantageous for generating a field vector in the vicinity of the patch 619, for mapping electric field propagation across the surface of the subject, etc.

Figure 6E:
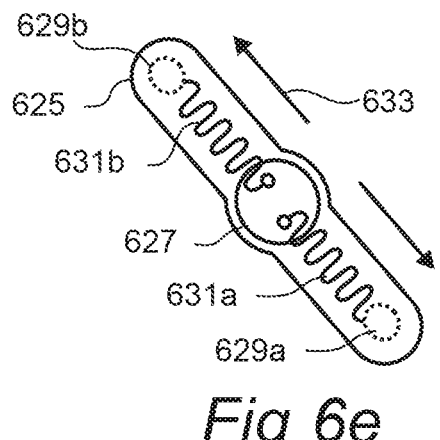

FIG. 6e shows a patch 625 coupled to a module 627 each in accordance with the present disclosure. The patch 625 includes a plurality of electrodes 629a, 629b for interfacing with a subject. The electrodes 629a, 629b are shown in a bipolar arrangement connected to stretchable conducting elements 631a, 631b. In aspects, such a configuration may be advantageous to freely flex and stretch 633 along with the nearby tissues of the subject during a monitoring and/or stimulating session. The stretchable conducting elements 631a, 631b may be arranged so as to repeatably change impedance during stretch. Alternatively or in combination, a thin stretchable dielectric element may be arranged between two or more layered conducting elements 631a, 631b and the impedance (i.e., capacitance) of the resulting structure measured with stretch. Such a configuration may be advantageous for assessing movement or local tissue stretch under the patch 625 (e.g., due to muscle movement, breathing, etc.) in conjunction with one or more physiologic signals (e.g., such as electrophysiological signals, stretch related artifact, etc.) in accordance with the present disclosure. Such a configuration may be suitable for physiotherapy monitoring sessions (e.g., combined proprioceptive monitoring in conjunction with EMG, assessing breathing in conjunction with ECG, gait assessment, a running gait correction system, etc.).

A non-contacting stimulating device may be, for example an audio and/or visual system, a heating or cooling system, etc. Smart speakers and smart televisions or other displays are examples of audio and/or visual non-contacting stimulation devices. A smart speaker, for example, may be used to provide audible stimulus to the subject in the form of an alert, a suggestion, a command, music, other sounds, etc. Other examples of non-contacting stimulation devices include means for controlling temperature such as fans, air conditioners, heaters, etc.

One or more stimulating devices may also be incorporated in other systems, such as stimulating devices integrated into a bed, chair, operating table, exercise equipment, etc. that a subject interfaces with. A bed, for example, may include one or more pneumatic actuators, vibration actuators, shakers, or the like to provide a stimulus to the subject in response to a command, feedback signal or control signal generated based on measurement of one or more physiologic parameters of the subject utilizing one or more sensing devices.

Although the disclosure has discussed devices attached to the body for monitoring aspects of the subject's disorder and/or physiologic information, as well as providing a stimulus, therapeutic stimulus, etc. alternative devices may be considered. Non-contacting devices may be used to obtain movement information, audible information, skin blood flow changes (e.g., such as by monitoring subtle skin tone changes which correlate with heart rate), respiration (e.g., audible sounds and movement related to respiration), and the like. Such non-contacting devices may be used in place of or to supplement an on-body system for the monitoring of certain conditions, for applying stimulus, etc. Information captured by non-contacting devices may, on its own or in combination with information gathered from sensing devices on the body, be used to direct the application of stimulus to the subject, via one or more stimulating devices on the body and/or via one or more non-contacting stimulating devices.

In some embodiments, aspects of monitoring the subject utilizing sensing devices in the modular physiologic monitoring system may utilize sensing devices that are affixed to or embodied within one or more contact surfaces, such as surfaces on a piece of furniture on which a subject is positioned (e.g., the surface of a bed, a recliner, a car seat, etc.). The surface may be equipped with one or more sensors to monitor the movement, respiration, HR, etc. of the subject. To achieve reliable recordings, it is advantageous to have such surfaces be well positioned against the subject. It is also advantageous to build such surfaces to take into account comfort level of the subject to keep the subject from feeling the sensing surfaces and to maintain use of the sensing surface over time.

Stimulating devices, as discussed above, may take the form of audio, visual or audiovisual systems or devices in the sleep space of the subject. Examples of such stimulating devices include smart speakers. Such stimulating devices provide a means for instruction a subject to alter the sleep state thereof. The input or stimulus may take the form of a message, suggestion, command, audible alert, musical input, change in musical input, a visual alert, one or more lights, a combination of light and sound, etc. Examples of such non-contacting stimulating devices include systems such as Amazon Echo®, Google Home® and the like.

Skeletal muscles are the principal effectors of mammalian (including human) motion and movement. Physical activity in mammals such as humans is derived from skeletal muscle, which connects either to additional muscle or to bone via ligaments. Molecular actin and myosin protein interaction in three dimensions causes muscle striation and cells to contract, facilitating virtually all movement in humans and other mammals. Muscle energetics obey physical laws regarding energy transduction, with conversion of biochemical energy into contractile or physical energy. Biochemical energy derives from glucose, which initiates a chain of conversion from chemical to mechanical energy.

Chemical energy from glucose may be derived from aerobic metabolism (e.g., O2 oxidation via glucose) or from anaerobic metabolism (e.g., glucose-based energy without oxygen via a lactic acid intermediate). Aerobic metabolism is more efficient, and is the primary pathway for muscle-derived energy.

Two pathways are involved in glucose metabolism, the anaerobic and aerobic processes. Aerobic metabolism occurs in mitochondria, and is the most efficient muscle means of energy conversion (e.g., biochemical to mechanical). Aerobic metabolism requires oxygen, while anaerobic metabo-lism occurs in the cytoplasm. Anaerobic metabolism is markedly less efficient than aerobic metabolism.

Anaerobic metabolism involves blood-borne glucose diffusing into cellular cytoplasm with immobilization and activity through phosphorylation. Glucose molecules are converted to fructose, which is re-phosphorylated to fructose diphosphate. These are energy-requiring steps (e.g., two adenosine triphosphates (ATPs) per glucose molecule). Fructose is cleaved into two glyceraldehyde phosphates (GPs).

Biochemical energy is released as two ATPs and two NADHs (nicotinamide adenine dinucleotide (NAD)+hydrogen (H)), as oxidized to phosphoglycerates. In the final stages, two additional ATPs are produced as phosphoglycerates are oxidized to pyruvate. These ATPs are the biochemical currency of metabolism and energy.

Aerobic metabolism pyruvate is at the initial point in the process for oxidative phosphorylation via the Krebs citric acid cycle. In this process, all carbon-carbon (C—C) and carbon-hydrogen (C—H) bonds of the pyruvate are transferred to oxygen. The process is more efficient in energy generation than anaerobic glycolysis.

Optimal energy efficiency and muscle output is thus critically dependent on O2 and glucose delivery via blood supply to the functioning muscle. This equates to volumetric blood flow into muscle, which delivers both glucose and oxygen.

Muscle quantitative blood supply is critical to high muscle mechanical energy output, especially in athletics or other needs for bodily motion. Blood supply is a function of blood volume delivery over time (cardiac output, 1/min) and the intramuscular vascular peripheral resistance (mmHg/flow in mmHg/ml/min). Muscle inefficiency or failure can result from improper matching of pressure-flow to peripheral resistance.

Cardiovascular fitness and all physical activity are directly derived from the above-described energy cycles. The ability of the heart and lungs to deliver adequate oxygen and glucose to skeletal muscles during exercise is the principal function of the heart and conductance vessels. Each heartbeat ejects a volume of blood into the aorta, which subsequently flows throughout the body. Cardiac blood output may be measured in liters of blood per minute. Stroke volume is the metric used for blood delivery (e.g., volume of blood from each heartbeat). Stroke volume multiplied by heart rate yields cardiac output. If this volumetric blood (e.g., cardiac output) is insufficient to meet muscle and oxygen requirements, muscles cannot function at optimal performance and athletic results are impaired in comparison to their potential if greater blood delivery were available.

Insufficient blood volume is similarly a problem in failing hearts. In such cases, the stroke volume and cardiac output are typically impaired, and the bodily musculature does not receive enough blood to allow normal, everyday activity.

One important physiologic parameter is vascular resistance. If vascular resistance is lowered in failure, improved blood perfusion results and a patient improves clinically. A primary function of modern heart failure medication is to increase heart energetics to improve stroke volume and systemic pressure, and to lower peripheral vascular resistance to permit added blood flow through the peripheral vascular resistance.

Failing hearts with low cardiac output can be improved with contractility enhancement, via inotropic agents that increase the strength of cardiac contraction. Cardiac output can also be increased by vasodilator drugs, which are pharmacologic agents that manipulate small resistance blood vessels causing them to relax and increase blood flow. Dilated microvasculature and improved cardiac contractility/inotropy are thus key components to increased oxygen and glucose delivery to active muscle.

Mechanical devices may be used to provide assistance to a subject to increase blood volume and blood flow, and to optimize pressure using external energy sources. Some mechanical devices, such as the total artificial heart and left ventricular assist device (LVAD), function through increased inotropy. Other mechanical devices include intra-aortic balloon pumps (IABPs). An IABP is an inflated-deflated cycled/pressurized balloon that is placed in the peripheral aorta, whose expansion and contraction is timed with the heartbeat. The balloon of an IABP inflates and deflates very rapidly, often using helium (because of its low density) and very high speed inflation/deflation cycling. Effective balloon pump use requires precision timing for inflation and deflation, and uses surface electrocardiogram (ECG) for synchrony. The balloon must expand during diastole when the aortic valve is closed, and rapidly deflate or contract prior to or at ventricular systole when the aortic valve is opened or opening. This fine-tuning reduces cardiac afterload, and assists with ejection as a result of finely adjusted inflation-deflation timing.

The inflation-deflation cycles and sequences are effective for augmenting blood flow and/or blood pressure with rapid inflation-deflation in the distal aorta, accomplishing two positive results. First, inflation assists blood flow, by expanding the balloon and pumping blood. Inflation occurs in diastole with the aortic valve closed. Deflation occurs with aortic vale opening causing markedly decreased afterload resistance, making the heart workload less as the deflation creates a lower pressure region that propagates. The net result is increased cardiac output at comparable or reduced myocardial energy consumption, since a better match has been made possible by the external energy source. Such assist devices permit more muscle glucose and oxygen delivery, derived from an external energy source via improved matching and addition of timed energy delivery.

In some embodiments, techniques are provided for technologic and physiologic vascular afterload reduction in precise synchrony with cardiac pressure-volume bolus, for improving muscle energetics.

The microvasculature of the body is composed of highly compliant, highly compressible reservoirs of blood. The microvasculature includes arteries, arterioles, capillaries, venules and veins. Such vascular structures are ubiquitous in the body, especially in large musculature of the limbs and body core.

Many of the blood vessels within skeletal muscle are compressed during skeletal muscle contraction and open during muscle relaxation. Compression by skeletal muscle effects an antegrade pressurization, which augments the cardiac output since compression is used for muscle blood flow augmentation in some embodiments.

The compliant multi-vessel microvascular and macrovascular reservoir is located before, at and distal to muscle cells, so that increased flow via alternating tissue compression-release enhances blood flow. This is, in effect, a physiologic "turbo charger" that augments and enhances the heart for delivery of oxygen and nutrients to muscle tissue.

Periodic compression and relaxation of the microvascular blood vessel networks, when precisely timed and in appropriate synchrony with cardiac output (e.g., cardiac pressure-flow bolus), provides multiple advantages. Such advantages include significant afterload reduction, lessening the workload of the heart since a comparable blood flow is achieved with the same or less cardiac work. Such advantages also include active blood pumping along the natural vascular pressure gradient of arteries and veins. The hemodynamic and hydrodynamic effects are analogous to those achieved with an external balloon pump, with afterload reduction occurring as the vascular system expands following compression. Active systolic pumping of cardiac output or blood bolus down the arterio-venous blood gradient further assists the heart in antegrade pumping, amplifying the turbo-charging effect by augmenting pressure and flow with energy or power from the skeletal muscle.

In some embodiments, techniques include signaling a subject for voluntary feedback to initiate contraction or relaxation of skeletal muscle (e.g., in the legs, arms, core, etc.). This signaling is performed in real-time (e.g., such as via the use of one or more stimulating devices in a modular physiologic monitoring system described herein). The signaling is timed using various physiologic parameters such as ECG, heart rate, breathing or other physiologic signals (e.g., measured or monitored using one or more sensing devices in a modular physiologic monitoring system described herein). Notifications for feedback are provided to a subject to give appropriate timing for activity (e.g., contraction or relaxation of skeletal muscle).

The activity may vary based on a particular use case scenario or operating environment. For example, the activity may relate to contraction and/or relaxation of a particular muscle group or groups during a specific user activity. In running, for instance, the activity may include timing a foot striking the ground or lifting from the ground. In cycling, the activity may relate to pedal rotation and phase. When the pedal is at its apex the musculature is relaxed and the large vessels (e.g., the ilio-femoral aggregate system) have dilated, and when the pedal is at its pedigree the muscle(s) have contracted, pushing blood into its capillaries. Other examples of user activity where contraction and relaxation of muscles may be timed include but are not limited to skating, walking, other motions for applications involving heart failure, etc.

More generally, embodiments may be used in any of a wide variety of user activities where there is an optimal muscle contraction in a cycle that can be used to improve performance, improve cardiovascular output, etc. Feedback may be provided to the user so as to influence or adjust a timing onset of a muscle contraction or relaxation, a contraction intensity, a lack of antagonist muscle contraction, a duration of muscle contraction, a timing of a deactivation of a muscle in the cycle, minimization of muscle activity during an off period of the cycle, etc. Feedback may be provided to any of a wide variety of muscles or regions, such as primary muscles, antagonist muscles, secondary muscles (e.g., muscles that are active but not the primary muscle for a given activity), etc.

In some embodiments, the power and/or energy arising from skeletal muscle is applied to the vasculature by precision sensing of the cardiac bolus. Various physiologic parameters may be used for precision sensing of the cardiac bolus, including but not limited to ECG, pressure waves, hemoglobin saturation, skin-muscle hemoglobin saturation, etc. Timing signals or other stimulus are provided to the subject, permitting coordination of user activity to perform desired augmentation, to adjust biomechanics, to prevent or encourage the use of cheater muscles, etc. In some embodiments, a goal is to adjust the biomechanics of a cyclic motion or gait (e.g., such as to keep forces through a knee of a subject centered to limit knee injuries). Preventing or encouraging the use of cheater muscles may be used in various stages of a workout or other user activity session (e.g., to discourage the use of cheater muscles early in the session, to encourage the use of cheater muscles later in the session, etc.).

Techniques described herein allow skeletal muscle to simultaneously assist and strengthen the effect of the heart-beat for improved energy efficiency and muscle enhance-ment effects. Techniques described herein may also or alternatively be used to enhance biometrics during user activity. In such cases, systems may be configured to moni-tor muscle activity and an event (e.g., an impact event such as the impact of a foot against the ground) timed against the contraction of one or more muscles (e.g., in the leg of the subject) during the activity. For example, timing may be established between two events (e.g., the impact event and contraction of the muscles) so as to minimize the impact on the foot as the step is completed. Feedback mechanisms may be configured to stimulate a subject at a reflex-compensated time, so as to adjust the muscle contraction to better relieve the impact of the step during user activity.

In some embodiments, it may be desired to synchronize events that do not have the same period. As one example, consider respiration of a subject and pedal position during a cycling activity. In this example, the respiration of the subject and the pedal position may have different periods or cycles. In these and other scenarios the events with different periods may be synchronized to achieve a desired result. Continuing with the above example, such a desired result may be to synchronize the start of inspiration with the left leg of the subject being at a particular pedal position in the motion of the pedaling cycle. The timing of the synchroni-zation may be selected so as to maximize blood flow to the leg of the subject, to minimize diaphragmatic effort (e.g., which may be tracked utilizing a sensor located on an abdomen of the subject), etc. Generally, embodiments may seek to provide feedback or stimulus to synchronize two or more events to maximize or increase a desired output with reduced effort on the part of the subject.

In some embodiments, systems may be configured to monitor limb or torso movement during user activity, and to actively signal the subject in real-time so as to limit or adjust such movements to improve efficiency during the user activity.

Decreased peripheral resistance improves myocardial energetics, with lower energy expenditure for comparable myocardial work in antegrade/forward blood flow. Afterload reduction, when timed and effected using techniques described herein, reduces aortic blood volume during car-diac diastole and instead directs blood into the muscle for greater oxygen and glucose delivery. Synchrony with ejec-tion reduces heart afterload, since blood is ejected into a low resistance. The effect is to increase myocardial efficiency using skeletal muscle energy not only with mechanical shortening but also in microvascular compression. Stiffening or shortening increases intramuscular pressure proportional to the strength of the muscle contraction.

In some embodiments, a key secondary effect is to squeeze intramuscular capillaries, which augments capillary flow from arteries to capillaries to veins. A majority of intravascular volume is in the microvasculature, and peri-odic skeletal muscle contraction causes compression and resistance directly proportional to intramuscular contraction. In the setting of a subject using muscles randomly (i.e., without feedback as described herein related to muscle contraction), negative impact on performance is possible. In this case, the cardiac blood bolus arrives at the large vessels and microvasculature when they are compressed, creating stress on the vessel and wasting myocardial energy. Skeletal muscle contraction is thus out of synchrony with cardiac ejection, and causes myocardial contraction against closed peripheral arteries and microvasculature. This results in: (i) marked negative impact on both muscle and heart efficiency; (ii) hearts and vessels being exposed to excess pressure without flow or with lower flow; (iii) poor and inefficient flow into the muscle; (iv) skeletal muscle receiving less blood and at lower pressure, limiting its function; etc.

Modular physiologic monitoring systems in some embodiments include one or more sensing and/or stimulat-ing devices, which take advantage of periodic skeletal muscle contraction to synchronize with heartbeat. The sens-ing devices are configured to sense the timing of myocardial ejection, and the stimulating devices are configured to provide feedback to the subject in response to synchronize muscle contraction. Advantageously, systems provide for a substantive decrease in afterload and increased muscle blood flow by periodic, timed skeletal muscle contraction and relaxation that is synchronized with appropriate timing through feedback sensing of the heart bolus and ejection.

An integrated modular physiologic monitoring system disclosed herein may function to increase stamina and enhance cardiovascular efficiency by appropriate timing of cardiac ejection and muscle synchrony during a user activity. Muscle synchrony in the example user activity of cycling involves the subject wearing sensing and/or stimulating devices of a modular physiologic monitoring system receiv-ing a real-time indicator of ejection and an electromyo-graphic indicator of muscle contraction. The subject can use this feedback to consciously coordinate muscle contraction with ejection, optimized to a timing delay. The delay may be timed based on feedback such as EMG, capillary or skin O2 saturation, etc.

In some embodiments, monitoring systems include com-ponents for sensing cardiac ejection, for sensing muscle contraction, and for defining algorithms for timing of feed-back to a subject.

Several techniques can be used for sensing the ambient timing of an aortic blood bolus, including through the use of ECG measurements. Electrical detection of any of a variety of electrocardiographic components may be used for sensing the timing of the aortic blood bolus, such as using sensed ECG components including then QRS complex, R-wave, P-wave, T-wave etc. Other techniques for sensing the timing of the aortic blood bolus include using modules or sensors configured for multichannel sensing. In such cases, modules with multichannel sensing may be configured to measure multiple parameters of a subject simultaneously to assess heart function, ejection timing, etc. In some embodiments, a module or sensor may include hardware configured to measure both an ECG and precision accelerations on a site on the torso of a subject. The ECG signal may be used to evaluate the timing of various electrical activities of the heart, while simultaneously the accelerations may be used to assess mechanical activities of the heart including ejection timing from the left ventricle. In this example, the accelera-tions may provide a precision ballistocardiogram. The pre-cision and/or noise floor of the accelerometers used to measure acceleration may be better than 150 ug/sqHz, better than 100 ug/sqHz, or better than 50 ug/sqHz to support capture of the ballistocardiogram.

The ballistocardiogram (BCG) may be characterized as follows. The waveform may be divided into three groups, generally labelled with letters: pre-ejection (FGH), ejection (IJK) and the diastolic part of the heart cycle (LMN). In this way, the waveform of the BCG represents the different phases of the full cardiac cycle. The peak of the H-wave is localized at the end of the contraction phase of the heart and the onset of the rapid expulsion of the blood from the heart into the aorta. The I-wave reflects the rapid acceleration of blood into the ascending aorta, pulmonary trunk and carotid arteries. The J-wave describes the acceleration of blood in the descending and abdominal aorta, and the deceleration of blood in the ascending aorta. The I-J amplitude reflects the force of contraction of the left ventricle, and the I-J interval reflects its contractility.

In one non-limiting example, the BCG and ECG may be collected simultaneously and compared. The timing between waves in the ECG and the BCG may be established under conditions of various posture, resting or post activity states (e.g., such as just before and just after running on a treadmill). Then, during periods of intense activity, the ECG waveforms may be used to establish approximate timing of the BCG waveforms in the case that the accelerations due to the activity are sufficiently large so as to make capture of the BCG impractical during the activity. Further an algorithm relating the ECG to the BCG may adaptively and opportunistically monitor the overall acceleration amplitudes and posture of the subject (e.g., from precision accelerometers), and determine periods of limited movement wherein the relationship between the ECG waveforms and BCG waveforms may be assessed throughout a given workout or activity. Such a configuration may be advantageous to establish timing of cardiac events (both electrically and mechanically) throughout the cardiac cycle of the subject. These can then be related to the activity, and through one or more algorithms described herein, provide feedback to a subject so as to synchronize activities and physiological events to maximize performance while minimizing effort of the subject in that activity.

In another non-limiting example, a module may include a phonograph so as to capture a cardiac and/or respiratory phonocardiogram or phonopneumogram live with the ECG. Thus valve closing/opening events and/or respiratory events may be evaluated in real-time alongside the ECG waveforms, so as to correlate mechanical events in the heart against electrical event timing. In the same context as the BCG, this may allow for relative timing of these events to be established under various conditions. Then the ECG may be relied upon during periods of heavy movement in order to establish the timing base irrespective of the movement needed from the subject during the activity.

A timing delay algorithm may be used to account for the delay that exists between electrical excitation and mechanical contraction. Delay timing with a variable sensing is typically in the range of 0-300 milliseconds (ms) between electrical systole (e.g., QRS complex) and ejection (e.g., vascular blood flow). Incorporating delay timing allows for optimization of muscle contraction by the subject.

In some embodiments, capillary filling is used for sensing. Using feedback provided by monitoring systems described herein, a subject may time and synchronize EMG readings of peak muscle activity to coincide with an optimized time delay after myocardial systole to coincide with left ventricle (LV) ejection. At this time, the subject is at maximum relaxation (e.g., in cycling this corresponds to the downstroke of one leg, in running this corresponds to ground contact with one leg, etc.). This fills the open vessels of one leg. In the next cycle, the muscles of that leg contract (which may be monitored using EMG or other physiologic parameters) and eject blood forcefully from the vessel system to the cells and through the vessels. In the next cycle, the opposite effect occurs, with the contralateral leg/muscles peak contraction ejecting blood into the relaxed vasculature. Each ejection is thus aided by natural smooth muscle relaxation, and muscular contraction aids in shifting blood into the contralateral vessel. The subject can thus cyclically and alternately aid blood flow into the vasculature, and alternately shunt blood away from contracting legs, limbs or muscles, by timing maximum relaxation using feedback provided from systems described herein. While described above with respect to cycling and running, similar techniques may be applied for various other activities, including other activities involving leg muscle movement such as skating.

In some embodiments, the inflow of saturated blood is detected by measuring hemoglobin (Hgb) saturation. As muscles contract and relax, there is a cyclic rise in the local Hgb saturation. Blood inflow may also or alternatively be detected using plethysmography by analyzing muscle/limb volume and size changes.

Systems described herein may provide for sensing of muscle contraction, such as skeletal or other muscle contraction through the use of one or multiple sensors. Such sensors provide capability to integrate and optimize determinations in real time. EMG sensors may be used to measure electrical based depolarization yielding a single contraction. Volumetric sensors may be used to measure volume of an extremity, limb or other region of a subject. As blood flows into an extremity or limb, its associated volume will increase slightly.

Accelerometers may also be used for sensing muscle contraction for various activities, such as running and other erect sports. In the case of running and other erect sports, resistance rises as either (or both) of the right and left extremities (e.g., feet, shins, knees, etc.) strike the ground. This rise or peak may be synchronized to the bolus ejection as detailed herein. Accelerometers may detect such activity by measuring the body or extremity center of mass. In some cases, the body center of mass may yield the best timing for the injection of fluid. Embodiments, however, are not limited solely to use with measuring the body center of mass. In running, skating and other activities, a foot striking the ground generates a reflected wave related to a gravitational field and the long artery in this field.

In one non-limiting example, the electromyogram of a local muscle group may be monitored with a sensor or sensors simultaneously with local accelerations. The EMG allows for real-time monitoring of the muscle activity, intensity, fatigue, onset of muscle tremor, onset of lactic acidosis in the muscle group, analysis of fast and slow twitch muscle fibers in the muscle, etc. while the accelerometers allow for real-time assessment of movement, onset of muscle tremor, delays between electrical activation and corresponding movement, etc. Such features and relative timing between features may be used as targets for synchronization, for analysis of biomechanics of a motion, for assessment of muscle activity throughout a motion, and optimization of any feature or relative timing thereof throughout the activity.

In some embodiments, light may be a sensed parameter used for timing. In such embodiments, a laser or other optic source (e.g., a light-emitting diode (LED), multiple wavelengths, etc.), infrared (IR) or optical spectrometry can detect when an extremity is filling with blood. Reflectivity and colorimetric assessments may also be used in some embodiments. Ultrasound may also be used. An ultrasound beam may be used as a transducer for sensing various features of active muscle to voluntarily modulate stiffness, compliance, thickness, reflection, reflectivity, specularity, etc. Such features may be used for timing purposes described herein.

In some embodiments, techniques are used to adjust timing of feedback to a subject so as to program delays, or to accelerate relative muscle activation (e.g., conscious subject activity) to blood bolus (e.g., heart ejection). Embodiments may also provide for real time interval adjustment. Optimal results may be sensed using Hgb saturation or muscular contraction to define optimal configurations for cardiac optimization feedback. The cardiac optimization feedback to the subject is designed to optimize blood flow to a maximum value. The cardiac optimization feedback to the subject may be provided to the subject in real time, with scanning of subject physiologic parameters across varied timing intervals including continuous scanning, periodic scanning, etc. Systems described herein can sense optimal timing for the feedback, which may change over time, and adjust the timing of delivery of feedback to the subject to provide flow optimization.

As discussed above, physiologic monitoring systems in some embodiments are configured to provide feedback to the subject so as to initiate conscious or volitional synchrony of skeletal muscle activity (e.g., contraction, relaxation) with blood bolus ejection. Advantageously, this results in marked cardiac afterload reduction, inclusion of low resistance. Such synchrony obviates systole occurring during high peripheral resistance, and has the advantages of preserving vessel health by preventing fibrosis that occurs during repetitive motion. Synchrony can also lower intravascular pressure while maintaining the same or increased flow. Thus, some embodiments provide methods for vascular impedance matching.

Physiologic monitoring systems described herein provide feedback to a subject to preserve and enhance cardiac efficiency by informing the subject as to whether a change in motion would provide increased cardiorespiratory efficiency. Further, feedback adds a degree of cardiac-skeletal muscle efficiency interaction to improve performance at the same or less cardiac energy expenditure. Other physiologic parameters that can be improved using techniques described herein include respiration, respiratory quotient (e.g., $O_2/CO_2$), anaerobic threshold level, etc.

Other important interactions include skeletal muscle and systemic efficiency. Feedback provided using techniques described herein allow a subject to understand how close the subject is to his or her maximum energy expenditure at the current degree and timing of an activity. Similarly, techniques described herein facilitate willfully adjusting skeletal muscle contraction time according to heartbeat, ejection or bolus arrival in an organ or tissue, etc. based on sensing of various physiologic parameters of the subject.

Systems described herein may provide feedback to the subject in various ways. In some embodiments, feedback is provided to the subject by audio or acoustic signaling, such as using audible sounds that gives the user guidance as to when muscle contraction is optimal. The audio or acoustic signaling may be notified by pitch, amplitude, sounds related to harmonics, pleasing versus unpleasant sounds, binary (e.g., off-on), etc., and the audio or acoustic signaling may be modulated in frequency, amplitude, pulse width modulation, harmonics, etc. Feedback may also or alternatively be provided to the user visually, such as with a light or lights having varying amplitude, color, frequency modulation, etc. In some embodiments, feedback may be provided as a haptic feedback stimulus whereby the subject feels a sensation indicating appropriate or optimal synchrony. Such haptic feedback may be virtual or real, as with vibration, pain, temperature (e.g., heat/cold or its perception), etc. Haptic feedback may be delivered in varying quantity to provide different indications to the subject. For example, low to high amplitude may have qualities such as sharp to dull sensation stimulus, hot to cold sensation stimulus, pain to pleasant stimulus, etc. The haptic feedback may provide physical sensation to the user to time skeletal muscle activity via vibration, off-on stimulus, frequency, pulse width modulation, amplitude, harmonic content, etc.

In some embodiments, a process for providing feedback to a subject to initiate conscious or volitional synchrony of skeletal muscle activity with blood bolus ejection includes monitoring one or more kinematic and/or myographic signals from a first site on a subject and monitoring one or more cardiologic and/or respiratory signals from a second site on the subject, such as utilizing one or more sensing devices described herein. This monitoring may take place, for example, while the subject is performing a repetitive task such as running, cycling, skating, etc. as described herein. The monitored signals are analyzed to identify one or more events, such as a first event related to the kinematic and/or myographic signals and a second event related to the one or more cardiologic and/or respiratory signals. Such events may be detected during each instance of the repetitive task. For example, the first event may include identifying when a subject's foot strikes the ground while running. This event is detected repeatedly as the subject runs. Similarly, the second event may include identifying breathing or cardiologic actions (e.g., heartbeats, blood bolus ejection, etc.) as the user performs the repetitive task. Timestamps are generated for the first event and the second event. The timestamps in some cases are generated for each instance of the first event and the second event. An optimal timestamp for providing a feedback signal to the subject to enhance cardio-pulmonary performance of the subject is calculated utilizing the generated timestamps for the first event and the second event. The feedback signal is then provided to the subject, based on the optimal timestamp, using one or more stimulating devices as described herein.

While various embodiments are described herein with respect to targeting enhancements in cardio-pulmonary performance of the subject during an activity, embodiments are not limited solely to enhancing cardio-pulmonary performance of the subject. In some embodiments, the timing of feedback signals is determined to target biomechanical enhancement in movement of the subject during an activity in addition to or as an alternative to enhancing cardio-pulmonary performance. Targeting biomechanical enhancements is relevant for a wide variety of user activities, including most sporting or other athletic activities. For example, in golf there are ideal swing mechanics for a subject that have associated muscle activation timings, hand grip intensity, etc. that lead to implementation of the ideal swing (e.g., which can be measured via one or more kinematic sensors). Alternatively, for a particular activity there may be certain muscles or muscle groups that should not activate to enhance biomechanical movement. In such cases, strategically located feedback devices on the subject may be used to apply negative feedback or stimulus during subject movement to train the subject not to activate particular muscles or muscle groups, to alter patterns of breathing (e.g., such as related to golf swing timing, etc.). These and other biomechanical enhancements can be key parameters that improve subject performance dramatically during an activity (e.g., a golf swing, the course of a game, workout or other activity session, etc.). Thus, embodiments may seek to provide improvement in biomechanical performance of a subject in addition to or in place of improvements in cardio-pulmonary performance.

Further, while various embodiments are described with respect to measuring physiologic parameters at two or more sites on a subject, embodiments are not so limited. In some embodiments, multiple sensors or actuators may be co-located on a given site on a subject, with a first one of the multiple sensors measuring a first set of features or physiologic parameters and a second one of the multiple sensors measuring a second set of features or physiologic parameters. For example, the first sensor may measure a first feature of an activity (e.g., when a limb reaches an apex of a cycle on a bicycle) while the second sensor measures a second feature of the activity (e.g., activation of a muscle group in the thigh of the subject). In this example, a system may be configured to determine timing of and provide a feedback signal that is timed, after compensation for reflex delays, to align a timestamp of the first feature to a timestamp of the second feature so as to coordinate events associated with the first and second features. In some embodiments, it is desired to time kinematic requirements against myographic activations, intensities, durations, etc. to optimize efficiency or performance of an activity by a subject.

The first event may correspond to one or more of a muscle activity level, onset of a muscle contraction, relaxation of a muscle, peak contraction of a muscle, fatigue of a muscle, peak force generation by a muscle, peak myographic activity of a muscle, peak high frequency myographic activity of a muscle, peak fast twitch activity of a muscle, peak slow twitch activity of a muscle, etc. The monitored myographic signals may be related to one or more muscles selected from one or more of the following muscle groups: muscles on the torso, muscles on the back, muscles on the abdomen, muscles on a limb, arm, leg, foot, face, neck, pelvis, smooth muscle activity (e.g., GI smooth muscle, cardiac muscle, diaphragm muscle, etc.). Some target muscles in the leg include upper leg muscles, anterior muscles, posterior muscles, iliacus, psoas major and psoas minor, quadriceps, rectus femoris, vastus lateralis, vastus medialis, vastus intermedialis, hamstrings, biceps femoris, adductor brevis, gracilis, semimembranosus, semitendinosus, adductor longus, adductor magnus, sartorius, piriformis, gluteus maximus, gluteus medius, gluteus minimus, lower leg muscles, gastrocnemius, soleus, peroneus longus, peroneus brevis, tibialis anterior, tibialis posterior, extensor digitorum longus, extensor hallucis longus, flexor digitorum longus, peroneus tertius, digitorum brevis, abductor halluces, achilles tendon, flexor hallucis longus, etc. It should be appreciated that embodiments may be used for various other target muscles, including target muscles in the torso, back, face, arm, hand, foot, etc. of a subject. With the appropriate positioning of sensors, any muscle group in the body may be targeted (e.g., for therapy, athletics, etc.).

The first event may also or alternatively correspond to one or more kinematic or kinetic movements of the first site on the subject. Such kinematic or kinetic movements of the first site may include one or more of peak horizontal acceleration, peak horizontal velocity, minimum vertical acceleration, minimum vertical velocity, apex of an arc, an impact, a directional impact, a free fall condition, one or more joint movements including but not limited to abduction (protraction), adduction (retraction), depression, elevation, rotation (e.g., including upward (superior rotation) and downward (inferior rotation)), pronation, supination, etc.

The monitored cardiologic or respiratory signals may be varied as described herein, such as depending on the sensors used and their placement on the subject. In some embodiments, one or more features of a respiratory signal may be suitable for timing against in terms of an activity (e.g., a cyclic activity performed at a substantially superharmonic, equivalent, or subharmonic frequency associated with the respiration), and/or to synchronize a respiratory feature against a movement, muscle activation, etc. Some non-limiting examples of respiratory features include inhalation, exhalation, automatic pause of almost no breathing, tidal volume (the depth of inhalation), breathing frequency, inhalation rate, exhalation rate, respiratory effort, respiratory muscle activity (intercostal muscle, diaphragmatic muscle activity, etc.), etc.

In some embodiments, the first site (from which the kinematic and/or myographic signals are monitored) and the second site (from which the cardiologic and/or respiratory signals are monitored) may be co-located on the subject. In other embodiments, the first site and the second site may be on different locations of the subject, or may be external to the subject such as on a contacting surface, etc. The first site, for example, may be located on an appendage, an arm, a leg, a foot, a thigh, a knee, a calf, an ankle, a bicep, an elbow, a forearm, a wrist, an abdomen, or a pelvis of the subject. The second site, for example, may be located on a torso, a rib cage, an abdomen, a neck, a head, an ear, under an arm, or on an appendage of the subject. In some cases, the first site is on a machine interfaced with the subject.

The repetitive task may include running, walking, cycling, lifting a weight, jumping, squatting, sit-ups, crunches, head movement, rowing, swimming, swinging an implement, stair climbing, stretching, relaxing, punching, kicking, diving, twisting, tapping, typing, etc.

In some embodiments, calculating the optimal timestamp (e.g., for providing feedback or stimulus to the subject) may take into account various parameters or influencing factors. Such parameters or influencing factors include but are not limited to environmental factors, task related factors, fatigue and subject related factors, etc. which have an influence on the optimal timing of a relationship between events (e.g., when feedback should be signaled relative to the first and second events that are identified based on monitoring).

Some non-limiting examples of environmental factors include ambient temperature, light, pressure, local wind velocity/direction, movement over a mapped region, environmental obstacles, etc. These and other environmental factors may influence the reflexes of a subject, the optimal biomechanics of a movement, optimal movement rates for a given task, etc.

Some non-limiting examples of task related factors include the biomechanics of the given task (or movements within a task including movement rate), the type of repetitive motion being executed, the changes to the task as dictated by an overall plan for the activity, etc. In one non-limiting example, the task may include cycling on a bicycle, and a task related factor may include a change in gear on the bicycle during use. Such a change may alter the rate at which a muscle group may need to work, shorten or lengthen the timing between a measurable trigger and when the optimal synchronization point is meant to be reached in a cycle, etc.

Some non-limiting examples of fatigue/subject related factors include, particular features of the subjects anatomy (e.g., size, limb length, strength limitations, etc.), factors related to reflexes of the subject, factors related to attention (e.g., timing related changes witnessed by a system observer relating to the actual response time between giving the subject a trigger and recording the response thereof), factors related to fatigue (e.g., timing related changes that come on when one or more muscle groups on the subject have entered into a state of fatigue, when changes in biomechanics of a movement indicate a loss in precision related to a state of fatigue), movement related to a loss of attention from the subject (e.g., lack of responsiveness to a trigger, movement unrelated to the activity under study, etc.), etc.

In some embodiments, a training procedure is used to establish an optimum delay between detection of the first and second events (e.g., the timestamps associated with such events) and the optimal timestamp when feedback should be signaled to the subject. The optimum delay may be task-dependent (e.g., the optimum delay may vary based on whether the user is running, cycling, rowing, etc.). Generally, the training procedure may involve changing the stimulus or other feedback provided to the subject while monitoring various parameters of the subject to look for an increase or decrease in one or more cardiologic performance metrics. Monitoring of the subject may take place from cycle to cycle while the subject performs the repetitive task, so as to optimize over time (e.g., time averaged optimization). In some cases, the optimization may be performed for a cycle N, with the optimal stimulus timing starting on a next cycle N+1 (or another cycle N+M).

The repetitive task performed by the subject may change over time. Consider, for example, running or cycling, where the subject may be going uphill, downhill, into a headwind or aided by a tailwind, etc. The optimal timing or delay for providing the feedback stimulus to the subject may take into account such changes in the repetitive task performed by the subject.

In some embodiments, the repetitive task may refer to a longer-term task, such as a gymnastics or other sports routine, a ski jump, etc. In such cases, the optimal timestamp or other timing of the feedback provided to the subject may be coordinated within the longer-term task.

Various types of feedback may be used. Stimulating devices, as described herein, may be used to provide various types of stimulus or other feedback to a subject including but not limited to audio and/or visual feedback, heat/cold, vibration, electrical, mechanical, visual stimulus from a heads up display, from a dashboard, a handlebar display, a watch, a phone, or the like. In some non-limiting examples, feedback may be provided in the form of a haptic vibration provided from an actuator placed against the skin of the subject, located within a module as described herein, placed within a wearable device worn somewhere on the subject, or the like. In another non-limiting application, feedback may be provided in the form of a mild electrical shock (e.g., an electrical nerve stimulus, the waveform of which may be provided as described herein so as to provide a mild pain, shock, and/or to emulate a soft touch, a thermal stimulus, etc.), a tingling sensation, a sharp impulse, etc.

In some embodiments, stimulating devices may be placed on the subject at multiple locations, and the feedback or other stimulus may be provided to a particular location on the subject so as to optimize reflex time. For example, a device may be attached or placed on the subject at a location, such as at one of the locations highlighted in FIG. 1. In such a situation, the time delay associated with receipt and transmission of the input signal to the brain or relay center and back to the effector muscles will determine a time delay which may be accounted for when determining the ideal time at which to provide the stimulus in order to align the effector muscle response with a particular event in the activity. Test stimulus may be provided to the subject at multiple locations while monitoring the subject's response to determine the optimal location for providing feedback to the user to optimize reflex time.

Feedback intensity may be modulated, such as based on monitoring the subject's response to ensure that sufficient motivation is provided to the subject to achieve a desired response and increase cardio-pulmonary performance of the subject.

Reflexes of the subject may be calculated from the feedback site so as to adjust and determine the optimal delay between the timestamps of the first and second events and the optimal timestamp for providing feedback to the subject. For example, timing between when the feedback signal is sent to the subject and determining when the subject adjusts their movement related to the task may be measured to calculate reflex time of the subject. The reflexes of the subject may thus be accounted for in determining the optimal timestamp for providing feedback to the subject. The reflex response time may be continuously monitored, so as to alter the timing of feedback to account for changes in the subject related to fatigue or other factors described herein.

Figure 7A:
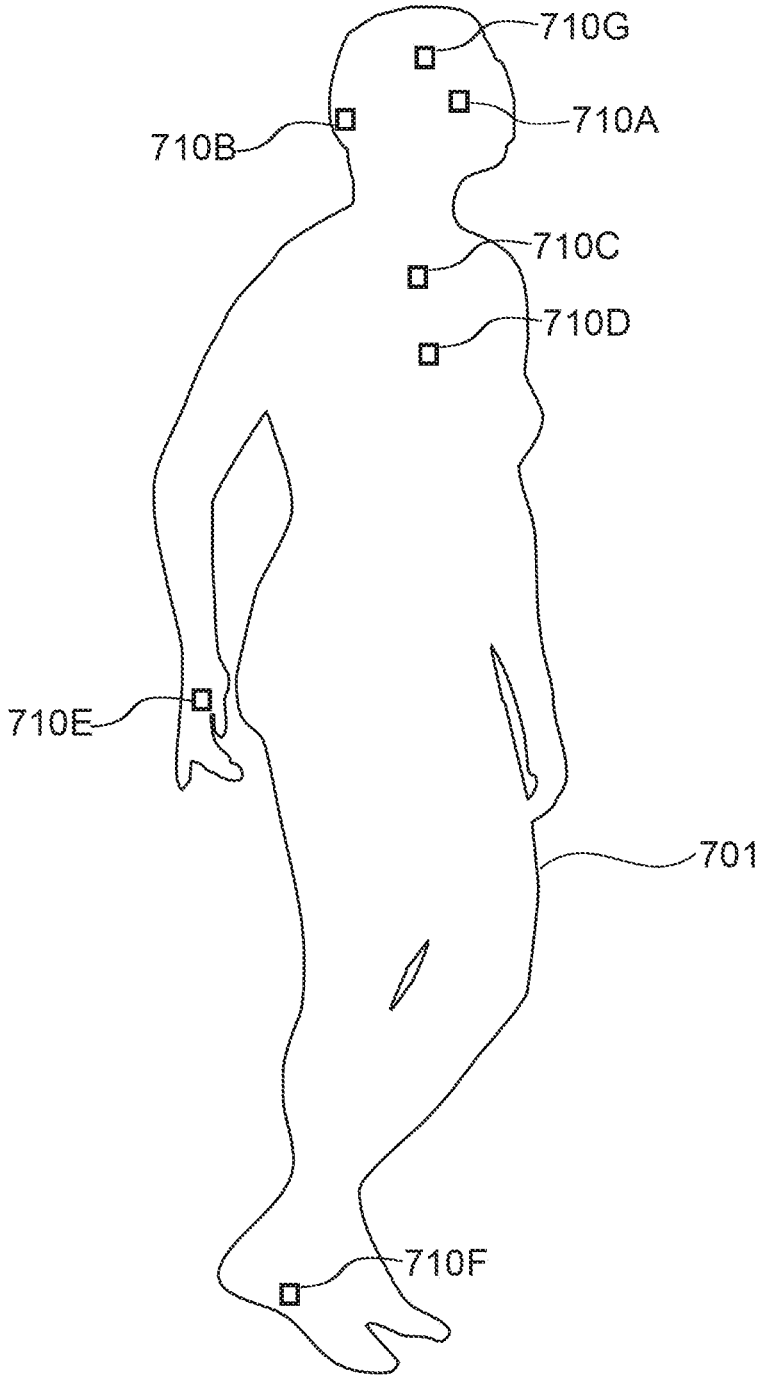
FIGS. 7a-7b illustrate placement of sensors on a subject and determining response to stimulus using the sensors, according to an embodiment of the invention.
Figure 7B:
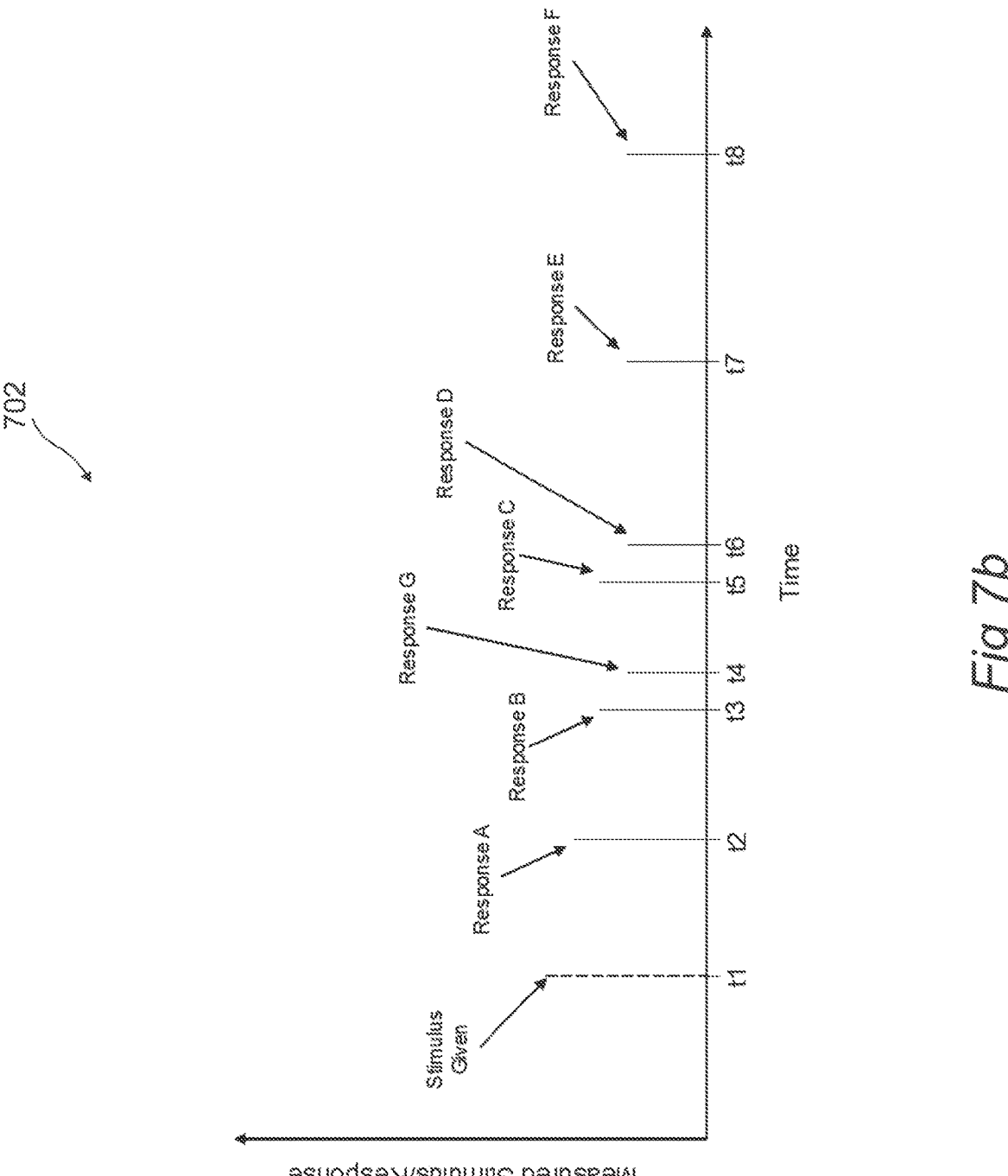

FIG. 7a illustrates a set of sensors or modules 710 attached to a subject 701 at various sites A-G. Each of the sensors 710 may represent a sensing device, a stimulating device, or a combination of a sensing and stimulating device. Sensor 710A is attached to site A on an eye or eyes of the subject 701, and may be a visual sensing/stimulating device. Sensor 710B is attached to site B on the ear of the subject 701, and may be an audible sensing/stimulating device. Sensor 710C is attached to site C on the chest of subject 701, and may be a tactile or haptic sensing/stimulating device. Sensor 710D is attached to site D on the chest of the subject 701, and may be an electrical sensing/stimulating device. Sensor 710E is attached to a site E on the hand of the subject 701. Sensor 710F is attached to a site F on the foot of the subject 701. Sensor 710G is attached to a site G on the face of the subject 701. FIG. 7b shows a plot 702 of stimulus to response time. The plot 702 shows a stimulus given at a time t1, with responses to the stimulus measured at the sensors 710 at sites A-G at times t2-t8, respectively. As illustrated, the subject 701 may have varying response times to the applied stimulus. The response time may vary based on a number of factors, such as the type of stimulus applied, the location of the applied stimulus, the focus of the subject 701, etc.

Figure 8A:
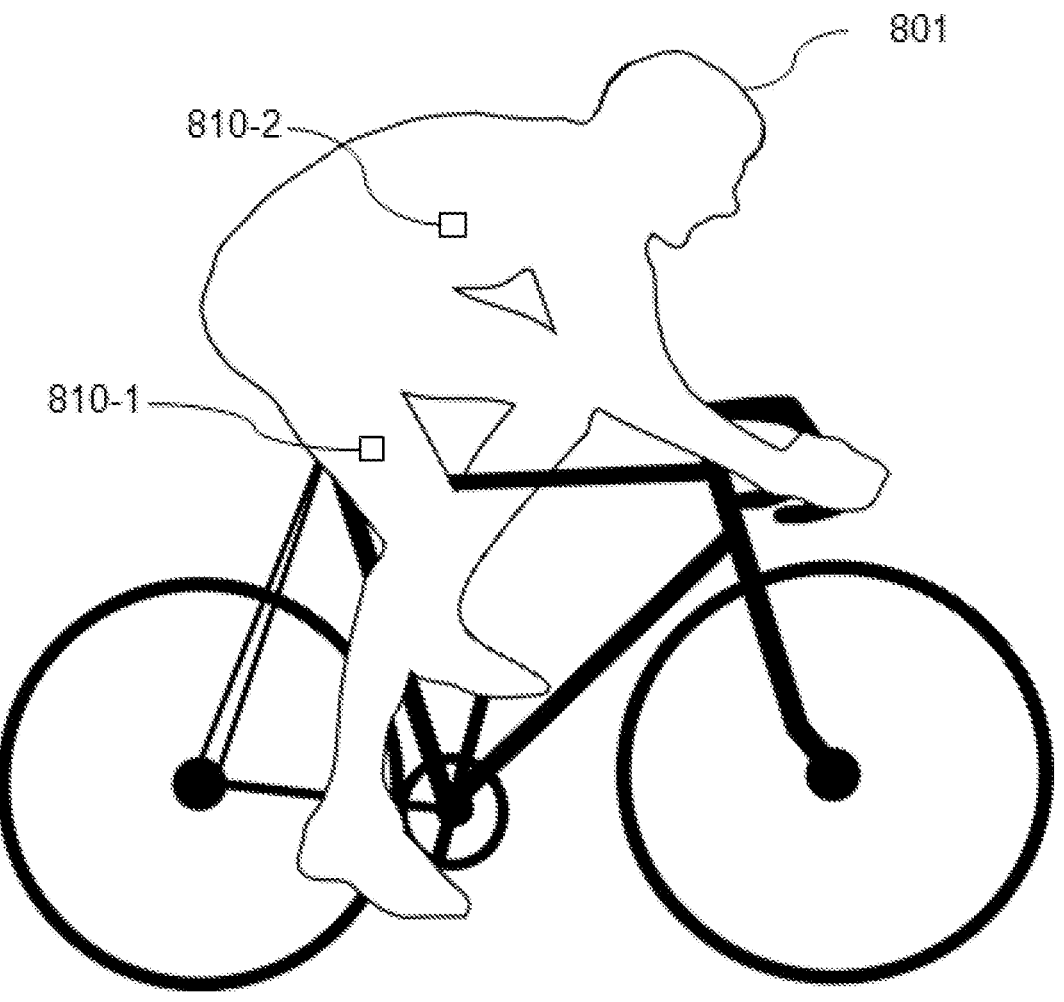
FIGS. 8a-8d illustrate placement of sensors on a subject during an activity along with plots detailing synchronization of feedback to improve performance of the subject during the activity, according to an embodiment of the invention.

FIG. 8a illustrates a subject 801 performing an activity, more particularly a cycle motion activity. Two sensors 810-1 and 810-2 are attached to the subject 801. The sensor 810-1 is attached to the thigh of the right leg of the subject 801, while the sensor 810-2 is attached to the chest of the subject 801. Each of the sensors 810-1 and 810-2 may represent a sensing device, a stimulating device, or a combination of a sensing device and a stimulating device. In the FIG. 8a example, the sensor 810-1 is more particularly configured to measure or monitor an EMG of muscles in the thigh of the right leg of the subject 801 while the sensor 810-2 is configured to measure or monitor heart rate or respiration of the subject 801.

Figure 8B:
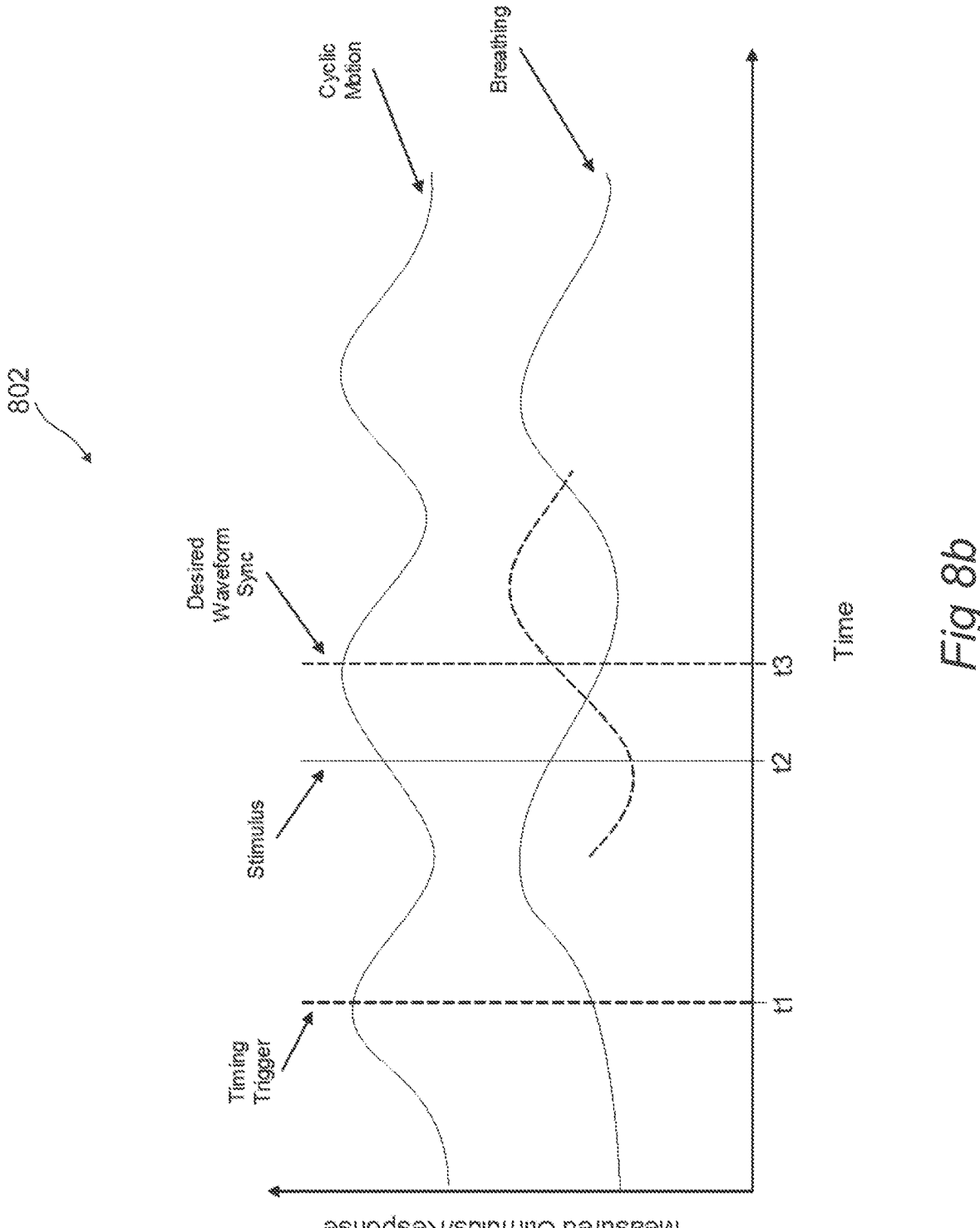

FIG. 8b shows a plot 802 for synchronizing breathing of the subject 801 during the cyclic motion of the subject 801 in FIG. 8a. The plot 802 shows a first curve (denoted "cyclic motion") indicating measurements of the sensor 810-1 attached to the thigh of the subject 801, and may represent movement or EMG trigger measurements of the cyclic motion. The plot 802 further includes a second curve (denoted "breathing") indicating measurements of the sensor 810-2 attached to the chest of the subject 801, and may represent HR, respiration or other physiologic parameters associated with breathing of the subject 801. The plot 802 shows a timing trigger (e.g., an apex of the first curve) at time t1 and an applied stimulus at time t2. The time delay between the timing trigger and application of the stimulus or feedback to the subject 801 may be determined using the techniques described herein. The plot 802 further shows a desired waveform synchronization of the second (breathing) curve with the first (cyclic motion) curve in dashed outline. The desired waveform synchronization is one in which cardio-pulmonary performance or other enhancement of the performance of the subject 801 during the activity is achieved.

The desired waveform synchronization or alignment between the first and second curves is created through application of an appropriately timed stimulus or feedback to the subject 801. In some embodiments, the desired waveform synchronization may be sub or super harmonic. The feedback or stimulus applied to the subject 801 creates a phase change so as to align waveforms of the first and second curves to the desired waveform synchronization. It should be appreciated that the application of stimulus or feedback to the subject 801 may be adapted over time during the activity. For example, a first or initial stimulus or feedback may be determined using estimates based on stimulation type, stimulation location, subject reflex timing and/or focus, etc. Such factors may be determined for a particular subject as described above with respect to FIGS. 7a and 7b and elsewhere herein. The stimulus phase timing is adjusted to better align results to achieve a desired response.

Figure 8C:
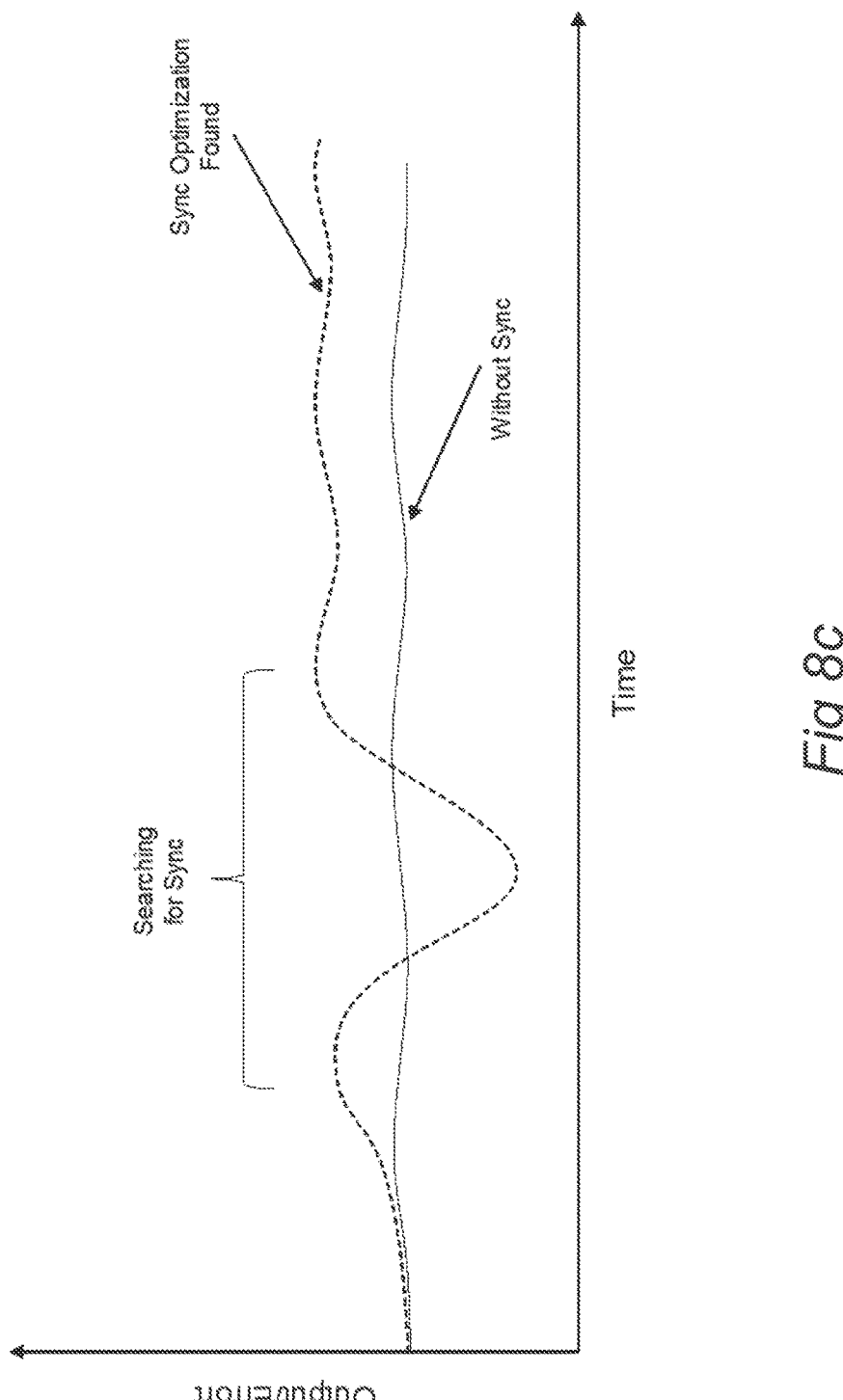

FIG. 8c shows a plot 804 of output/effort as a function of time, for a first curve (shown in solid line) and a second curve (shown in dashed outline). The first curve indicates a case without synchronization or without use of the techniques described herein for enhancing performance of the subject 801 during the activity, while the second curve indicates a case with synchronization or with use of the techniques describe herein for enhancing performance of the subject 801 during the activity. The output/effort is a measure of specified output and effort parameters of the subject 801 during the cycling activity. An example output parameter is speed, while example effort parameters include HR, respiration effort, muscle strain, muscle activation strength and/or duration per cycle, etc. The output and effort parameters may be measured using sensing devices described herein, such as sensors 810-1 and 810-2 on the subject 801. As a general matter, it is desired to increase the output while maintaining or reducing effort of the subject 801, or to maintain the output while decreasing the effort of the subject 801. During synchronization (e.g., such as that described above with respect to FIG. 8b and elsewhere herein), the second curve exhibits some fluctuation, possibly even having an output/effort worse than the first curve for some period of time. Once synchronization optimization is found, however, the use of techniques described herein permit for enhanced performance of the subject 801 (e.g., increased output/effort for the second curve relative to the first curve).

Figure 8D:
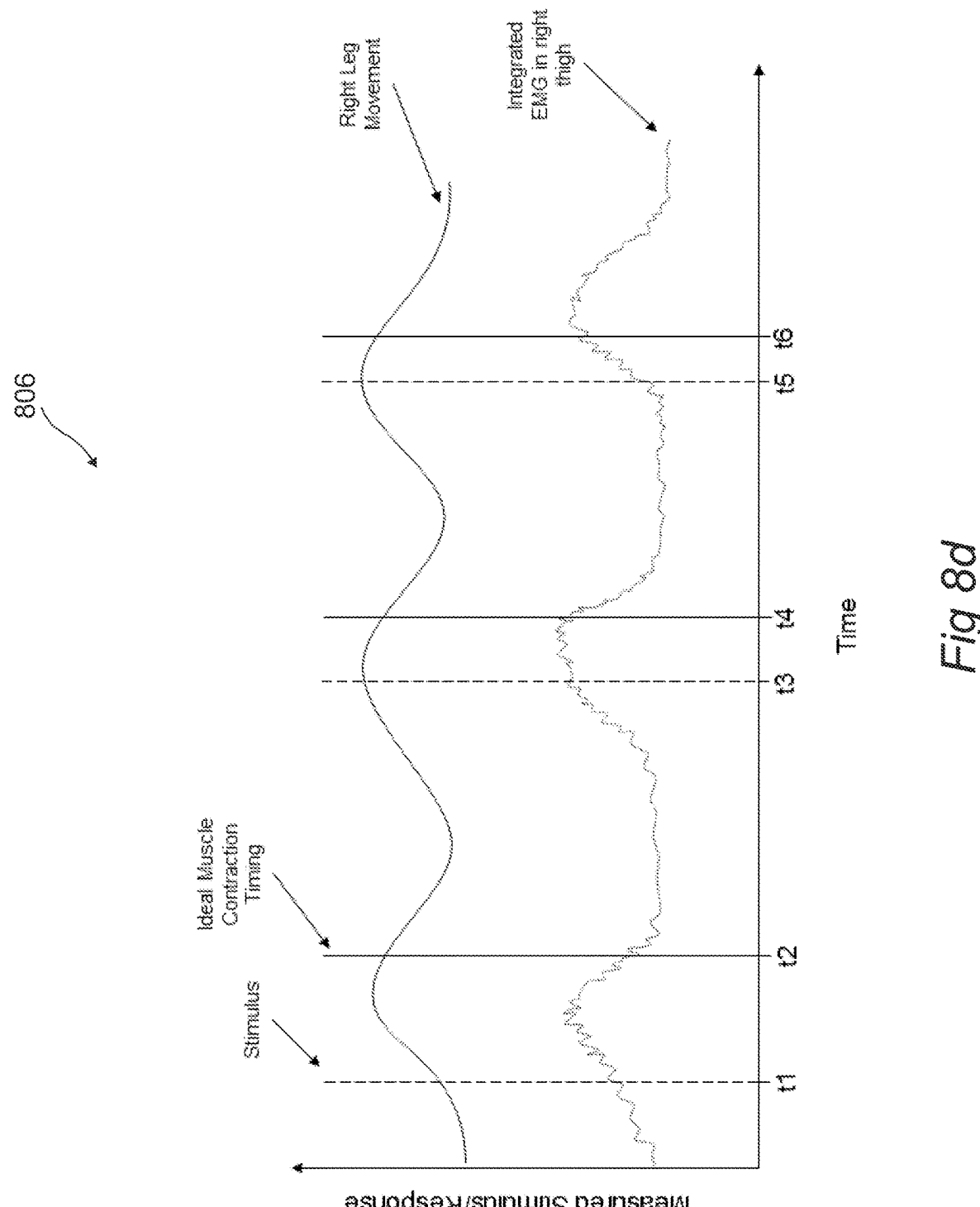

FIG. 8d shows a plot 806 of a measured stimulus/response of subject 801 over time during the activity. More particularly, the plot 806 shows a first curve of right leg movement of the subject 801 and a second curve of an integrated EMG in a right thigh of the subject 801. As shown, stimulus timing signals are applied at times t1, t3 and t5. The plot 806 further shows the ideal muscle contraction timing (e.g., in the right thigh of the subject 801 for enhancing performance) at times t2, t4 and t6. The plot 806 illustrates how muscle activation (e.g., in the right thigh of subject 801) may be correctly timed with a position (e.g., of the right leg of the subject 801) during the cyclic activity. In some embodiments, algorithms are used to adjust when the stimulus is given to the subject 801 so that the response timing is "ideal" for enhancing performance of the subject 801. In addition to or in place of optimizing muscle contraction timing, some embodiments may optimize muscle amplitude (e.g., intensity of contraction), push a duration of muscle contraction, end of push timing, etc. For a given activity, some embodiments may seek to optimize when in a particular cycle (e.g., rotation of the legs of the subject 801 while pedaling) the muscle contraction starts, the intensity of the contraction (e.g., a maximum voluntary isometric contraction), when in a particular cycle the muscle de-activates or relaxes, basal tone in the muscle during a particular cycle, etc.

Figure 9A:
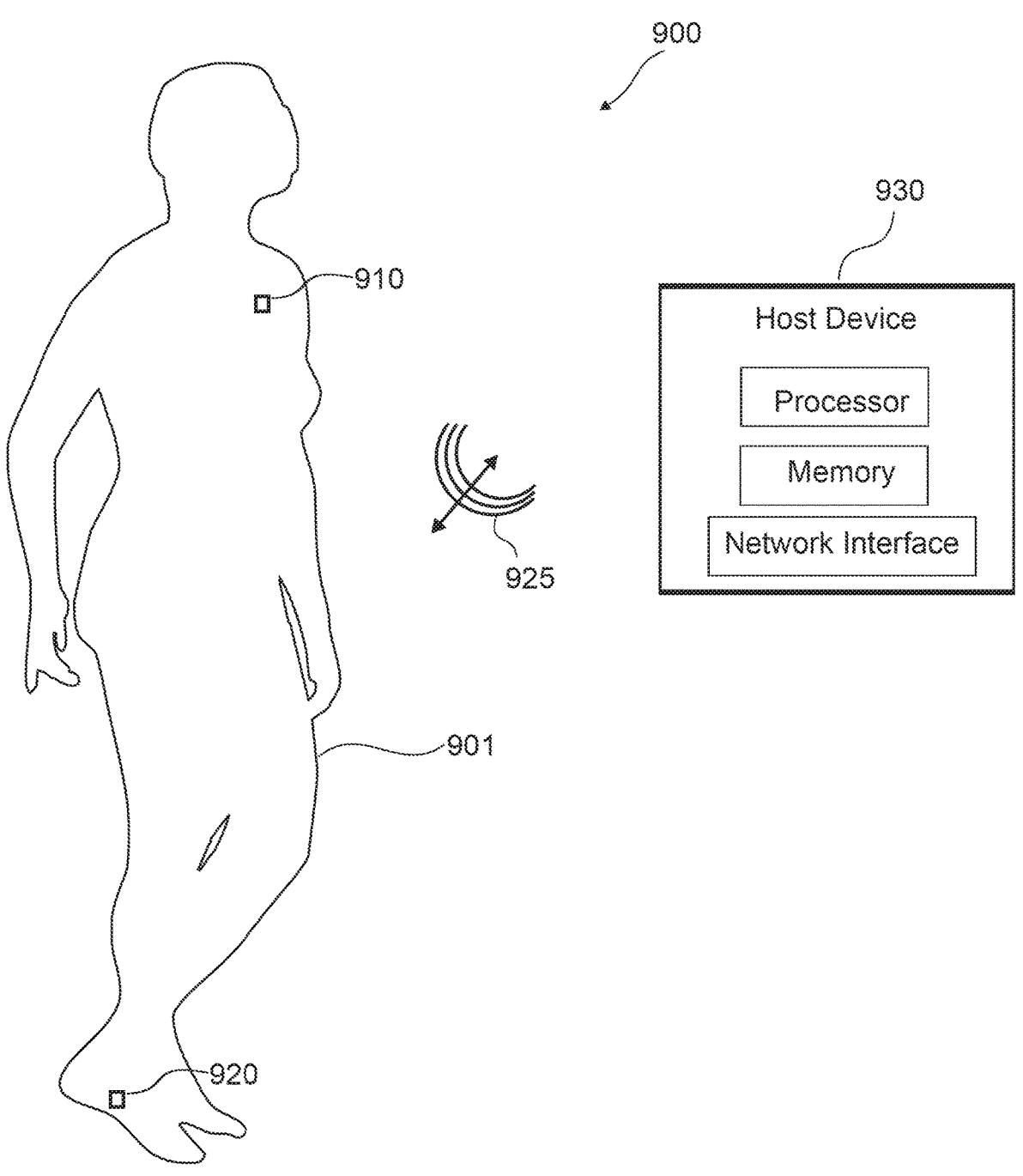
FIGS. 9a-9c illustrate a modular physiologic monitoring system, according to an embodiment of the invention.
Figures 9B, 9C:
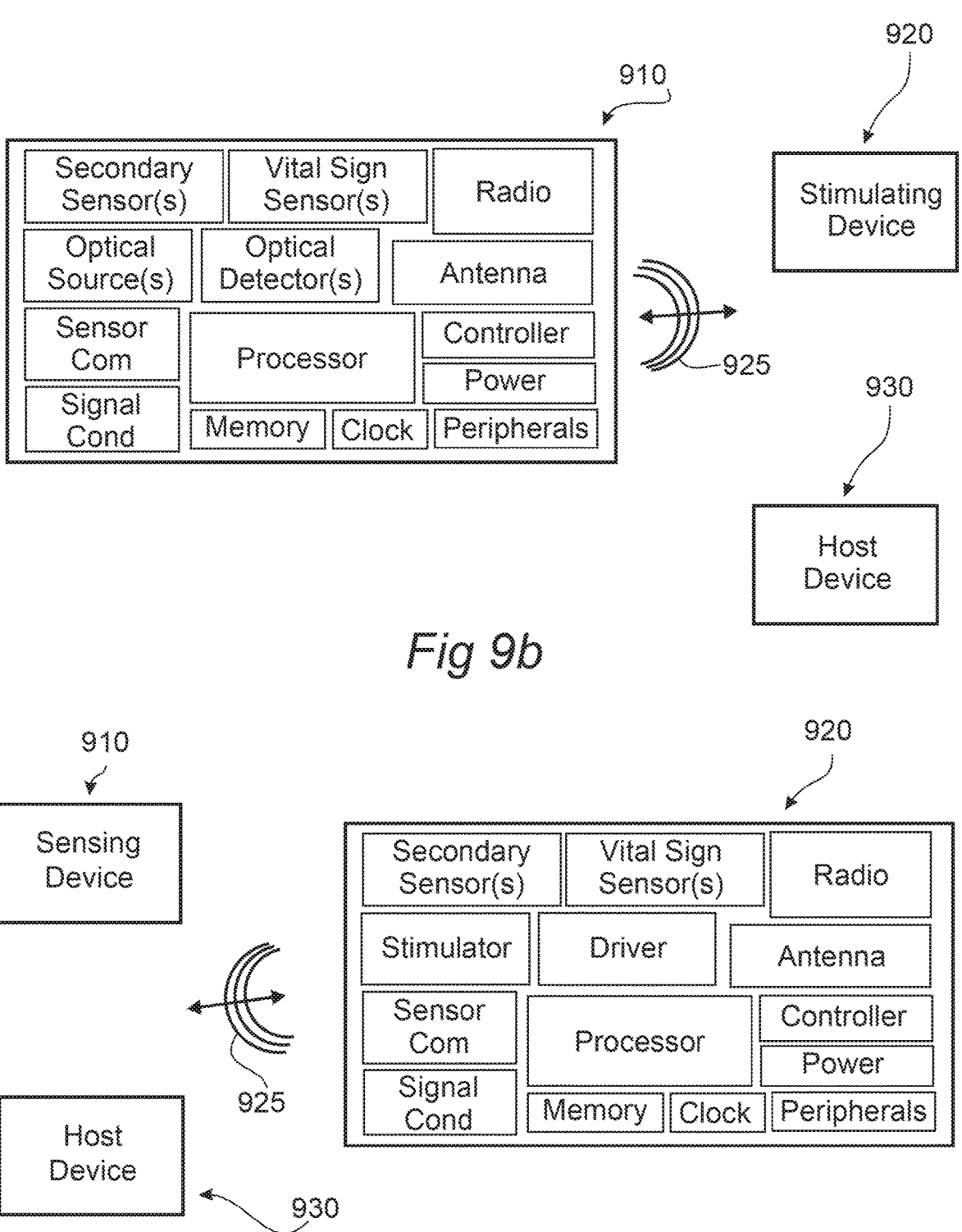

FIGS. 9a-9c show a modular physiologic monitoring system 900. The modular physiologic monitoring system 900 includes a sensing device 910 and a stimulating device 920 attached to a subject 901 that are in wireless communication 925 with a host device 930. The host device 930 includes a processor, a memory and a network interface.

The processor may comprise a microprocessor, a microcontroller, an application-specific integrated circuit (ASIC), a field-programmable gate array (FPGA) or other type of processing circuitry, as well as portions or combinations of such circuitry elements.

The memory may comprise random access memory (RAM), read-only memory (ROM) or other types of memory, in any combination. The memory and other memories disclosed herein may be viewed as examples of what are more generally referred to as "processor-readable storage media" storing executable computer program code or other types of software programs. Articles of manufacture comprising such processor-readable storage media are considered embodiments of the invention. A given such article of manufacture may comprise, for example, a storage device such as a storage disk, a storage array or an integrated circuit containing memory. The processor may load the computer program code from the memory and execute the code to provide the functionalities of the host device 930.

The network interface provides circuitry enabling wireless communication between the host device 930, the sensing device 910 and the stimulating device 920.

FIG. 9a illustrates a modular physiologic monitoring system 900 that includes only a single instance of the sensing device 910 and the stimulating device 920 for clarity. It is to be appreciated, however, that modular physiologic monitoring system 900 may include multiple sensing devices and/or multiple stimulating devices. In addition, although FIG. 9a illustrates a modular physiologic monitoring system 900 in which the sensing device 910 and the stimulating device 920 are attached to the subject 901, embodiments are not limited to such arrangements. As described above, one or more sensing and/or stimulating devices may be part of contacting surfaces or non-contacting devices. In addition, the placement of sensing device 910 and stimulating device 920 on the subject 901 may vary as described above. Also, the host device 930 may be worn by the subject 901, such as being incorporated into a smartwatch or other wearable computing device. The functionality provided by host device 930 may also be provided, in some embodiments, by one or more of the sensing device 910 and the stimulating device 920.

FIG. 9*b* shows a schematic of aspects of the sensing device 910 in modular physiologic monitoring system 900. The sensing device 910 includes one or more of a processor, a memory device, a controller, a power supply, a power management and/or energy harvesting circuit, one or more peripherals, a clock, an antenna, a radio, a signal conditioning circuit, optical source(s), optical detector(s), a sensor communication circuit, vital sign sensor(s), and secondary sensor(s). The sensing device 910 is configured for wireless communication 925 with the stimulating device 920 and host device 930.

FIG. 9*c* shows a schematic of aspects of the stimulating device 920 in modular physiologic monitoring system 900. The stimulating device 920 includes one or more of a processor, a memory device, a controller, a power supply, a power management and/or energy harvesting circuit, one or more peripherals, a clock, an antenna, a radio, a signal conditioning circuit, a driver, a stimulator, vital sign sensor(s), a sensor communication circuit, and secondary sensor(s). The stimulating device 920 is configured for wireless communication 925 with the sensing device 910 and host device 930.

Communication of data from the sensing devices and/or stimulating devices (e.g., patches and/or patch-module pairs) may be performed via a local personal communication device (PCD). Such communication in some embodiments takes place in two parts: (1) local communication between a patch and/or patch-module pair (e.g., via a hub or module of a patch-module pair) and the PCD; and (2) remote communication from the PCD to a back-end server. The PCD and back-end server may collectively provide functionality of the host device as described elsewhere herein.

Figure 10:
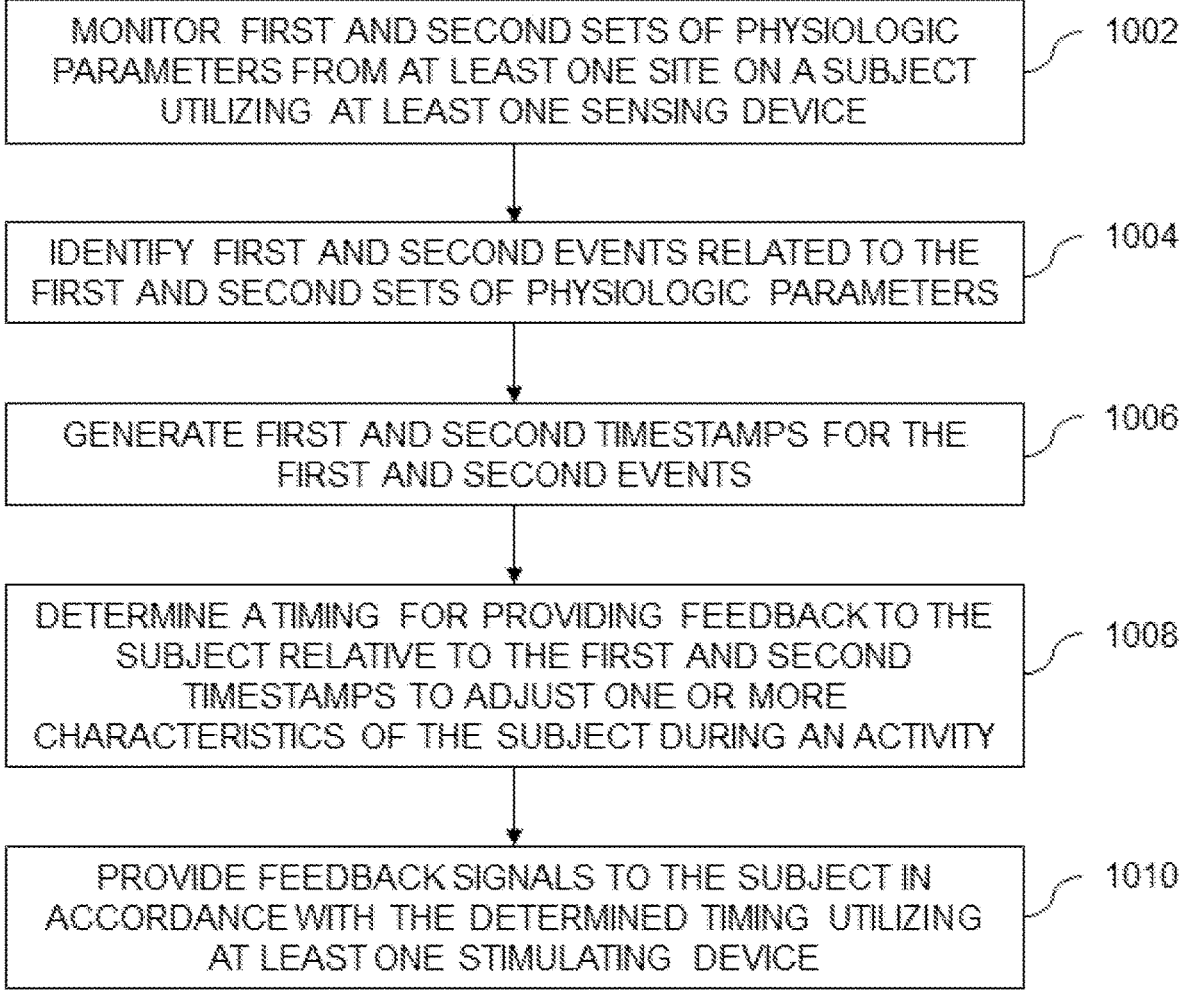
FIG. 10 illustrates a process flow for enhancing performance of a subject during an activity, according to an embodiment of the invention.

FIG. 10 shows a process flow for enhancing performance of a subject during an activity. The process flow begins with step 1002, monitoring first and second sets of physiologic parameters from at least one site on the subject utilizing at least one sensing device.

In some embodiments, the at least one sensing device includes a first sensing device attached to the subject at a first site and at least a second sensing device attached to the subject at a second site, where the first set of physiologic parameters are monitored at the first site utilizing the first sensing device and the second set of physiologic parameters are monitored at the second site utilizing the second sensing device. In some embodiments, the first and second sites may be co-located on the subject. In other embodiments, the first and second sites may be different. For example, the first site may be located on an appendage, an arm, a hand, a leg, a foot, a thigh, a knee, a calf, an ankle, a bicep, an elbow, a forearm, a wrist, an abdomen, or a pelvis of the subject, while the second site may be located on a torso, a rib cage, an abdomen, a neck, a head, an ear, under an arm, or on an appendage of the subject. In some cases, the first and/or second sites are on one or more machines interfaced with the subject.

The first set of physiologic parameters monitored in step 1002 may include at least one of one or more kinematic and one or more myographic signals from the first site on the subject, and the second set of physiologic parameters may include at least one of one or more cardiologic and one or more respiratory signals from the second site on the subject.

In some embodiments, the monitoring in step 1002 is performed while the subject performs a repetitive task. The repetitive task may comprise one of running, walking, cycling, lifting a weight, jumping, squatting, sit-ups, crunches, head movement, rowing, swimming, swinging an implement, and stair climbing.

The process flow continues with step 1004, identifying first and second events related to the first and second sets of physiologic parameters. The first event may correspond to at least one of: one or more muscle activity levels; onset of one or more muscle contractions; relaxation of one or more muscles; peak contraction of one or more muscles; fatigue of one or more muscles; peak force generation by one or more muscles; peak myographic activity of one or more muscles; peak high frequency myographic activity of one or more muscles; peak fast twitch activity of one or more muscles; and peak slow twitch activity of one or more muscles. The first event may correspond to one or more kinematic and kinetic movements, the one or more kinematic and kinetic movements comprising one or more of: a peak horizontal acceleration; a peak horizontal velocity; a minimum vertical acceleration; a minimum vertical velocity; an apex of an arc; a base of an arc; an impact; a directional impact; and a free fall condition. The second event may correspond to one or more events related to respiration or cardiac activity of the subject.

In step 1006, first and second timestamps are generated for the first and second events identified in step 1004. In step 1008, a timing for providing feedback to the subject relative to the first and second timestamps to adjust one or more characteristics of the subject during an activity is determined. Adjusting one or more characteristics of the subject during the activity may comprise enhancing cardio-pulmonary performance of the subject during the activity, providing biomechanical enhancement of movement of at least a portion of the subject during the activity, or both.

Step 1008 may be based at least in part on one or more environmental factors, one or more task-related factors for a repetitive task being performed by the subject, and one or more fatigue factors of the subject.

In some embodiments, step 1008 includes performing a training procedure comprising applying stimulus to the subject utilizing the at least one stimulating device and monitoring one or more physiologic parameters of the subject to determine one or more changes in at least one cardiologic performance metric and utilizing the determined one or more changes in the at least one cardiologic performance metric to determine an optimal timing for providing the feedback to the subject relative to the first timestamp and the second timestamp.

The process flow continues with step 1010, providing feedback signals to the subject in accordance with the determined timing utilizing at least one stimulating device. In some embodiments, the at least one stimulating device used in step 1010 is the same as the at least one sensing device used for monitoring in step 1002.

In some embodiments, the subject is performing a repetitive task comprising a plurality of cycles, and the monitoring in step 1002 is performed during two or more of the plurality of cycles so as to perform time averaged optimization for providing the feedback to the subject in step 1010 in response to first timestamps and second timestamps associated with first events and second events in each of the two or more cycles.

In some embodiments, the subject is performing a repetitive task comprising a plurality of cycles, and the monitoring in step 1002 is performed during a first one of the plurality of cycles and the feedback is provided in step 1010 in a second one of the plurality of cycles subsequent to the first cycle.

In some embodiments, the subject is performing a task comprising two or more activities during the monitoring in step 1002, and determining the timing for providing the feedback relative to the first timestamp and the second timestamp in step 1008 comprises coordinating the timing of the feedback for one or more designated activities within the task.

The feedback provided in step 1010 may comprise at least one of an electrical stimulus, a vibratory stimulus, an auditory stimulus, and a visual stimulus.

In some cases, the processing flow of FIG. 10 further includes applying a stimulus to two or more locations on the subject utilizing the at least one stimulating device, monitoring a response of the subject to the stimulus provided at each of the two or more locations utilizing the at least one sensing device, determining reflex times of the subject for stimulus applied to each of the two or more locations utilizing the monitored response, and selecting at least a given one of the two or more locations for providing the one or more feedback signals to the subject based on the determined reflex times.

In some embodiments, an intensity of the feedback provided in step 1010 is adjusted to achieve a desired cardiopulmonary performance enhancement level.

In some embodiments, the processing flow of FIG. 10 includes calculating one or more reflexes of the subject by monitoring the subject response relative to a timing of providing the one or more feedback signals to the subject to determine when the subject adjusts movement related to a task in response to the one or more feedback signals. Changes in reflex response time may be monitored, and the timing of providing the one or more feedback signals to the subject may be adjusted based on the one or more changes in the reflex response time of the subject.

It will be appreciated that additional advantages and modifications will readily occur to those skilled in the art. Therefore, the disclosures presented herein and broader aspects thereof are not limited to the specific details and representative embodiments shown and described herein. Accordingly, many modifications, equivalents, and improvements may be included without departing from the spirit or scope of the general inventive concept as defined by the appended claims and their equivalents.

What is claimed is:

1. An apparatus comprising:

a processor; and a memory coupled to the processor;

the processor being configured:

to monitor a first set of one or more physiologic parameters and a second set of one or more physiologic parameters from at least one site on a subject, wherein the first set of one or more physiologic parameters and the second set of one or more physiologic parameters are determined from electrophysiological signals captured utilizing at least one sensing device, the at least one sensing device comprising a skin-interfacing device comprising one or more skin-interfacing electrodes configured to capture the electrophysiological signals from which the first and second sets of one or more physiologic parameters are determined;

to identify a first event related to contraction or relaxation of skeletal muscle of the subject, the first event being identified utilizing the first set of one or more physiologic parameters;

to identify a second event related to cardiac output of a cardiac pressure-flow bolus of a heart of the subject, the second event being identified utilizing the second set of one or more physiologic parameters, wherein identifying the second event is based at least in part on correlating timing of electrocardiogram measurements determined from the captured electrophysiological signals characterizing electrical activities of the heart of the subject with ballistocardiogram measurements determined from the captured electrophysiological signals characterizing mechanical activities of the heart of the subject across two or more different postures, resting and activity states of the subject;

to generate a first timestamp for the first event and a second timestamp for the second event;

to monitor for one or more changes in one or more reflex response times of the subject across two or more subsequent additional instances of the first event and the second event while the subject is performing an activity comprising two or more tasks, wherein one or more of the subsequent instances of the second event are identified based at least in part on mapping electrophysiological measurements determined from the captured electrophysiological signals characterizing the electrical activities of the heart of the subject to ballistocardiagram measurements based at least in part on the correlated timing;

to determine, based at least in part on the monitored one or more changes in the one or more reflex response times of the subject and one or more biomechanic factors associated with a given one of the two or more tasks of the activity to be performed by the subject, a reflex-compensated timing for providing feedback to the subject in real time relative to timestamps of each of the two or more subsequent additional instances of the first event to adjust one or more characteristics of the subject during an activity to alter subsequent timing of the two or more subsequent additional instances of the second event relative to the two or more subsequent additional instances of the first event to increase muscle blood flow in the subject through synchronization of the contraction or relaxation of the skeletal muscle of the subject relative to the cardiac output of the cardiac pressure-flow bolus of each of two or more heartbeats of the heart of the subject; and to provide one or more feedback signals to at least one stimulating device associated with the subject in accordance with the determined reflex-compensated timing, wherein the at least one stimulating device comprises at least one of one or more skin-interfacing actuators and one or more skin-interfacing electrodes configured to apply at least one of a vibratory and an electrical stimulus to skin of the subject in real time relative to the timestamps of each of the two or more subsequent additional instances of the first event in response to the one or more feedback signals;

wherein adjusting the one or more characteristics of the subject during the activity to alter the subsequent timing of the two or more subsequent additional instances of the second event relative to the two or more subsequent additional instances of the first event comprises:

identifying, for the given one of the two or more tasks that the subject is performing, a target synchronization of respective instances of the first event and the second event; and determining the reflex-compensated timing to adjust timing of the two or more subsequent additional instances of the second event relative to the two or more subsequent additional instances of the first event to meet the identified target synchronization of respective instances of the first event and the second event.

2. The apparatus of claim 1, wherein adjusting one or more characteristics of the subject during the activity comprises enhancing cardio-pulmonary performance of the subject during the activity.

3. The apparatus of claim 1, wherein adjusting one or more characteristics of the subject during the activity comprises providing biomechanical enhancement of movement of at least a portion of the subject during the activity.

4. The apparatus of claim 1, wherein the at least one sensing device and the at least one stimulating device are the same.

5. The apparatus of claim 1, wherein the at least one sensing device comprises a first sensing device attached to the subject at a first site and at least a second sensing device attached to the subject at a second site, and wherein the first set of physiologic parameters are monitored at the first site utilizing a first subset of the electrophysiological signals captured utilizing the first sensing device and the second set of physiologic parameters are monitored at the second site utilizing a second subset of the electrophysiological signals captured utilizing the second sensing device.

6. The apparatus of claim 5, wherein the first site and the second site are co-located on the subject.

7. The apparatus of claim 5, wherein the first site is located on an appendage, an arm, a hand, a leg, a foot, a thigh, a knee, a calf, an ankle, a bicep, an elbow, a forearm, a wrist, an abdomen, or a pelvis of the subject.

8. The apparatus of claim 5, wherein second site is located on a torso, a rib cage, an abdomen, a neck, a head, an ear, under an arm, or on an appendage of the subject.

9. The apparatus of claim 5, wherein at least one of the first site and the second site are on at least one machine interfaced with the subject.

10. The apparatus of claim 5, wherein:

the first set of one or more physiologic parameters comprises at least one of one or more kinematic and one or more myographic signals from the first site on the subject determined from the first subset of the electrophysiological signals captured utilizing the first sensing device; and the second set of one or more physiologic parameters further comprises at least one of one or more cardiologic and one or more respiratory signals from the second site on the subject determined from the second subset of the electrophysiological signals captured utilizing the second sensing device.

11. The apparatus of claim 10, wherein the first event corresponds to at least one of: one or more muscle activity levels; onset of one or more muscle contractions; relaxation of one or more muscles; peak contraction of one or more muscles; fatigue of one or more muscles; peak force generation by one or more muscles; peak myographic activity of one or more muscles; peak high frequency myographic activity of one or more muscles; peak fast twitch activity of one or more muscles; and peak slow twitch activity of one or more muscles.

12. The apparatus of claim 10, wherein the first event corresponds to one or more kinematic and kinetic movements, the one or more kinematic and kinetic movements comprising one or more of: a peak horizontal acceleration; a peak horizontal velocity; a minimum vertical acceleration; a minimum vertical velocity; an apex of an arc; a base of an arc; an impact; a directional impact; and a free fall condition.

13. The apparatus of claim 1, wherein the activity comprises a repetitive task and wherein the two or more tasks comprises different instances of a same task.

14. The apparatus of claim 13, wherein the repetitive task comprises one of running, walking, cycling, lifting a weight, jumping, squatting, sit-ups, crunches, head movement, rowing, swimming, swinging an implement, and stair climbing.

15. The apparatus of claim 1, wherein determining the reflex-compensated timing is based at least in part on one or more environmental factors.

16. The apparatus of claim 1, wherein determining the reflex-compensated timing is based at least in part on one or more fatigue factors of the subject.

17. The apparatus of claim 1, wherein determining the reflex-compensated timing comprises:

performing a training procedure comprising applying said at least one of the vibratory and the electrical stimulus to the skin of the subject utilizing the at least one stimulating device and monitoring one or more physiologic parameters of the subject to determine one or more changes in at least one cardiologic performance metric; and utilizing the determined one or more changes in the at least one cardiologic performance metric to determine an optimal timing for providing the feedback to the subject relative to the timestamps of each of the two or more subsequent additional instances of the first event.

18. The apparatus of claim 1, wherein the repetitive task comprises a plurality of cycles, and wherein the processor is configured to perform the monitoring of the first and second sets of one or more physiologic parameters during two or more of the plurality of cycles so as to perform time averaged optimization for providing the feedback to the subject in real time relative to the timestamps of each of the two or more subsequent additional instances of the first event in each of the two or more cycles.

19. The apparatus of claim 1, wherein the repetitive task comprises a plurality of cycles, and wherein the processor is configured to perform the monitoring of the first and second sets of one or more physiologic parameters during a first one of the plurality of cycles and to provide the one or more feedback signals to the at least one stimulating device in a second one of the plurality of cycles subsequent to the first cycle.

20. The apparatus of claim 1, wherein the two or more tasks comprises a first task and at least a second task different than the first task, and wherein determining the reflex-compensated timing comprises determining a first reflex-compensated timing of the feedback for the first task and determining a second reflex-compensated timing of the feedback for the second task.

21. The apparatus of claim 1, wherein the processor is further configured:

to control the at least one stimulating device to apply said at least one of the vibratory and the electrical stimulus to two or more locations on the skin of the subject;

to monitor a response of the subject to the stimulus provided at each of the two or more locations utilizing the electrophysiological signals captured from the at least one sensing device;

to determine reflex response times of the subject for said at least one of the vibratory and the electrical stimulus applied to each of the two or more locations utilizing the monitored response; and to select at least a given one of the two or more locations for providing the one or more feedback signals to the subject based on the determined reflex response times of the subject for said at least one of the vibratory and the electrical stimulus applied to each of the two or more locations.

22. The apparatus of claim 1, wherein the processor is configured to adjust an intensity of the one or more feedback signals provided to the at least one stimulating device to achieve a desired cardio-pulmonary performance enhancement level.

23. The apparatus of claim 1, wherein the processor is configured to calculate the one or more reflex response times of the subject by monitoring the subject response relative to a timing of providing the one or more feedback signals to the at least one stimulating device to determine when the subject adjusts movement related to each of the two or more tasks in response to the one or more feedback signals.

24. The apparatus of claim 1, wherein the one or more biomechanic factors associated with the given task of the activity to be performed by the subject comprise at least one of one or more movements of the given task and a movement rate of the one or more movements of the given task.

25. The apparatus of claim 1 wherein determining the reflex-compensated timing is further based at least in part on an overall plan for a sequence of the two or more tasks of the activity.

26. A method comprising:

monitoring a first set of one or more physiologic parameters and a second set of one or more physiologic parameters from at least one site on a subject, wherein the first set of one or more physiologic parameters and the second set of one or more physiologic parameters are determined from electrophysiological signals captured utilizing at least one sensing device, the at least one sensing device comprising a skin-interfacing device comprising one or more skin-interfacing electrodes configured to capture the electrophysiological signals from which the first and second sets of one or more physiologic parameters are determined;

identifying a first event related to contraction or relaxation of skeletal muscle of the subject, the first event being identified utilizing the first set of one or more physiologic parameters;

identifying a second event related to cardiac output of a cardiac pressure-flow bolus of a heart of the subject, the second event being identified utilizing the second set of one or more physiologic parameters, wherein identifying the second event is based at least in part on correlating timing of electrocardiogram measurements determined from the captured electrophysiological signals characterizing electrical activities of the heart of the subject with ballistocardiogram measurements determined from the captured electrophysiological signals characterizing mechanical activities of the heart of the subject across two or more different postures, resting and activity states of the subject;

generating a first timestamp for the first event and a second timestamp for the second event;

monitoring for one or more changes in one or more reflex response times of the subject across two or more subsequent additional instances of the first event and the second event while the subject is performing an activity comprising two or more tasks, wherein one or more of the subsequent instances of the second event are identified based at least in part on mapping electrophysiological measurements determined from the captured electrophysiological signals characterizing the electrical activities of the heart of the subject to ballistocardiagram measurements based at least in part on the correlated timing;

determining, based at least in part on the monitored one or more changes in the one or more reflex response times of the subject and one or more biomechanic factors associated with a given one of the two or more tasks of the activity to be performed by the subject, a reflex-compensated timing for providing feedback to the subject in real time relative to timestamps of each of the two or more subsequent additional instances of the first event to adjust one or more characteristics of the subject during an activity to alter subsequent timing of the two or more subsequent additional instances of the second event relative to the two or more subsequent additional instances of the first event to increase muscle blood flow in the subject through synchronization of the contraction or relaxation of the skeletal muscle of the subject relative to the cardiac output of the cardiac pressure-flow bolus of each of two or more heartbeats of the heart of the subject; and providing one or more feedback signals to at least one stimulating device associated with the subject in accordance with the determined reflex-compensated timing, wherein the at least one stimulating device comprises at least one of one or more skin-interfacing actuators and one or more skin-interfacing electrodes configured to apply at least one of a vibratory and an electrical stimulus to skin of the subject in real time relative to the timestamps of each of the two or more subsequent additional instances of the first event in response to the one or more feedback signals;

wherein adjusting the one or more characteristics of the subject during the activity to alter the subsequent timing of the two or more subsequent additional instances of the second event relative to the two or more subsequent additional instances of the first event comprises:

identifying, for the given one of the two or more tasks that the subject is performing, a target synchronization of respective instances of the first event and the second event; and determining the reflex-compensated timing to adjust timing of the two or more subsequent additional instances of the second event relative to the two or more subsequent additional instances of the first event to meet the identified target synchronization of respective instances of the first event and the second event.

27. The method of claim 26, wherein adjusting one or more characteristics of the subject during the activity comprises at least one of: enhancing cardio-pulmonary performance of the subject during the activity; and providing biomechanical enhancement of movement of at least a portion of the subject during the activity.

28. A computer program product comprising a non-transitory processor-readable storage medium having stored therein executable program code which, when executed, causes at least one processing device:

to monitor a first set of one or more physiologic parameters and a second set of one or more physiologic parameters from at least one site on a subject, wherein the first set of one or more physiologic parameters and the second set of one or more physiologic parameters are determined from electrophysiological signals captured utilizing at least one sensing device, the at least one sensing device comprising a skin-interfacing device comprising one or more skin-interfacing electrodes configured to capture the electrophysiological signals from which the first and second sets of one or more physiologic parameters are determined;

to identify a first event related to contraction or relaxation of skeletal muscle of the subject, the first event being identified utilizing the first set of one or more physiologic parameters;

to identify a second event related to cardiac output of a cardiac pressure-flow bolus of a heart of the subject, the second event being identified utilizing the second set of one or more physiologic parameters, wherein identifying the second event is based at least in part on correlating timing of electrocardiogram measurements determined from the captured electrophysiological signals characterizing electrical activities of the heart of the subject with ballistocardiogram measurements determined from the captured electrophysiological signals characterizing mechanical activities of the heart of the subject across two or more different postures, resting and activity states of the subject;

to generate a first timestamp for the first event and a second timestamp for the second event;

to monitor for one or more changes in one or more reflex response times of the subject across two or more subsequent additional instances of the first event and the second event while the subject is performing an activity comprising two or more tasks, wherein one or more of the subsequent instances of the second event are identified based at least in part on mapping electrophysiological measurements determined from the captured electrophysiological signals characterizing the electrical activities of the heart of the subject to ballistocardiagram measurements based at least in part on the correlated timing;

to determine, based at least in part on the monitored one or more changes in the one or more reflex response times of the subject and one or more biomechanic factors associated with a given one of the two or more tasks of the activity to be performed by the subject, a reflex-compensated timing for providing feedback to the subject in real time relative to timestamps of each of the two or more subsequent additional instances of the first event to adjust one or more characteristics of the subject during an activity to alter subsequent timing of the two or more subsequent additional instances of the second event relative to the two or more subsequent additional instances of the first event to increase muscle blood flow in the subject through synchronization of the contraction or relaxation of the skeletal muscle of the subject relative to the cardiac output of the cardiac pressure-flow bolus of each of two or more heartbeats of the heart of the subject; and to provide one or more feedback signals to at least one stimulating device associated with the subject in accordance with the determined reflex-compensated timing, wherein the at least one stimulating device comprises at least one of one or more skin-interfacing actuators and one or more skin-interfacing electrodes configured to apply at least one of a vibratory and an electrical stimulus to skin of the subject in real time relative to the timestamps of each of the two or more subsequent additional instances of the first event in response to the one or more feedback signals;

wherein adjusting the one or more characteristics of the subject during the activity to alter the subsequent timing of the two or more subsequent additional instances of the second event relative to the two or more subsequent additional instances of the first event comprises:

identifying, for the given one of the two or more tasks that the subject is performing, a target synchronization of respective instances of the first event and the second event; and determining the reflex-compensated timing to adjust timing of the two or more subsequent additional instances of the second event relative to the two or more subsequent additional instances of the first event to meet the identified target synchronization of respective instances of the first event and the second event.

29. The computer program product of claim 28, wherein adjusting one or more characteristics of the subject during the activity comprises at least one of: enhancing cardio-pulmonary performance of the subject during the activity; and providing biomechanical enhancement of movement of at least a portion of the subject during the activity.

* * * * *